United States Patent
Sato et al.

(10) Patent No.: US 9,668,658 B2
(45) Date of Patent: Jun. 6, 2017

(54) MEASUREMENT APPARATUS

(71) Applicants: OMRON HEALTHCARE CO., LTD., Muko-shi, Kyoto (JP); Public University Corporation NARA MEDICAL UNIVERSITY, Kashihara-shi, Nara (JP)

(72) Inventors: Hironori Sato, Moriyama (JP); Naoki Mori, Takatsuki (JP); Tomoko Hashimoto, Suita (JP); Toshihiko Ogura, Inuyama (JP); Shozo Takamatsu, Nagaokakyo (JP); Hideo Utsuno, Suita (JP); Kimihiko Kichikawa, Kashihara (JP); Hirofumi Ito, Kashihara (JP)

(73) Assignee: OMRON HEALTHCARE CO., LTD., Muko (JP)

(*) Notice: Subject to any disclaimer, the term of this patent is extended or adjusted under 35 U.S.C. 154(b) by 817 days.

(21) Appl. No.: 13/718,413

(22) Filed: Dec. 18, 2012

(65) Prior Publication Data

US 2013/0109982 A1   May 2, 2013

Related U.S. Application Data

(63) Continuation of application No. PCT/JP2011/066340, filed on Jul. 19, 2011.

(30) Foreign Application Priority Data

Jul. 20, 2010   (JP) .................................. 2010-163113

(51) Int. Cl.
   *A61B 5/02*   (2006.01)
   *A61B 5/024*   (2006.01)
   (Continued)

(52) U.S. Cl.
   CPC ...... *A61B 5/02438* (2013.01); *A61B 5/02014* (2013.01); *A61B 5/0285* (2013.01);
   (Continued)

(58) Field of Classification Search
   CPC .............. A61B 5/02438; A61B 5/7225; A61B 5/02444; A61B 5/0285; A61B 5/02014; A61B 5/7246; A61B 5/6824
   (Continued)

(56) References Cited

U.S. PATENT DOCUMENTS

| 6,893,400 B2* | 5/2005 | Kawaguchi ........ A61B 5/02007 600/481 |
| 2004/0171940 A1 | 9/2004 | Narimatsu |
| 2010/0121204 A1* | 5/2010 | Utsuno .............. A61B 5/02007 600/485 |

FOREIGN PATENT DOCUMENTS

| JP | A-05-023335 | 2/1993 |
| JP | A-2004-261319 | 9/2004 |

(Continued)

OTHER PUBLICATIONS

Trachet, et al. "Numerical Validation of a New Method to Assess Aortic Pulse Velocity from a Single Recording of a Brachial Artery Waveform with an Occluding Cuff." Annals of Biomedical Engineering. Mar. 2010. vol. 38, No. 3. pp. 876-888.*

(Continued)

*Primary Examiner* — Tiffany Weston
(74) *Attorney, Agent, or Firm* — Oliff PLC

(57) ABSTRACT

A first calculation unit receives phase characteristics Pa(f) and Pb(f) outputted from frequency transform units, calculates a propagation time difference based on a phase difference between the two phase characteristics in a high-frequency component thereof, and calculates a pulse wave velocity by dividing a difference in the distances of vascular (Continued)

pathways from the heart to respective measurement areas. Meanwhile, a second calculation unit calculates a pulse wave velocity by dividing the stated difference in the distances by a appearance time difference at a predetermined position in respective pulse waveforms obtained by rendering the measurement signals Pa(t) and Pb(t) on a time axis. A comparison unit compares the pulse wave velocities, and in the case where the ratio thereof is outside a predetermined range, an evaluation result indicating that it is possible that a predetermined pathologic change is present in the vascular pathway is outputted to a display processing unit.

10 Claims, 15 Drawing Sheets

(51) Int. Cl.
  *A61B 5/0285*  (2006.01)
  *A61B 5/0295*  (2006.01)
  *A61B 5/00*  (2006.01)

(52) U.S. Cl.
  CPC ........ *A61B 5/0295* (2013.01); *A61B 5/02444* (2013.01); *A61B 5/7225* (2013.01); *A61B 5/6824* (2013.01); *A61B 5/6829* (2013.01); *A61B 5/7246* (2013.01)

(58) Field of Classification Search
  USPC .................................................. 600/490–504
  See application file for complete search history.

(56)      References Cited

FOREIGN PATENT DOCUMENTS

| | | |
|---|---|---|
| JP | A-2007-222626 | 9/2007 |
| JP | A-2008-246010 | 10/2008 |

OTHER PUBLICATIONS

Aug. 30, 2011 International Search Report issued in International Application No. PCT/JP2011/066340.

* cited by examiner

MEASUREMENT APPARATUS

This is continuation of application Serial No. PCT/JP2011/066340 filed Jul. 19, 2011, the contents of which are incorporated herein by reference.

BACKGROUND OF THE INVENTION

Field of the Invention

This invention relates to measurement apparatuses, and particularly relates to measurement apparatuses for evaluating the likelihood of a predetermined pathologic change in a vascular pathway.

Description of the Background Art

Aortic aneurysm can be given as an example of a predetermined pathologic change in a vascular pathway. An aortic aneurysm in the abdominal area in particular has no early symptoms, and unless unintentionally discovered during an MRI (magnetic resonance imaging system), a CT (computed tomography) scan, or the like, is often discovered just before rupture, during an abdominal surge or the like. It is therefore desirable to detect such a condition early through a casual examination, such as during a health checkup.

JP H5-23335A discloses, as an apparatus for detecting aortic aneurysms, an apparatus that makes diagnoses using ultrasound waves. Meanwhile, JP 2007-222626A discloses a method and apparatus that detect a specific site as a pathologic change by comparing multiple pieces of image data taken through X-ray CT, MRI, or the like.

However, with the ultrasound wave diagnostic apparatus disclosed in JP H5-23335A, it is necessary to take sequential measurements of the aorta based on the likelihood that an arterial aneurysm is present. On the other hand, the method and apparatus disclosed in JP 2007-222626A require that an image of the blood vessels throughout the entire body has been captured in advance through X-ray CT, MRI, or the like. In other words, the apparatuses, details of the examinations, and so on are elaborate with either technique. Accordingly, from the standpoint of time and costs, there is a problem in that it is difficult to detect, through health checkups or the like, individuals affected by aortic aneurysms from among many individuals. As a result, there are cases where an aortic aneurysm is discovered after it has worsened to the point where it can be detected through touch from the outside.

SUMMARY OF THE INVENTION

Having been achieved in light of the stated problem, it is an object of the present invention to provide a measurement apparatus capable of evaluating the likelihood of a predetermined pathologic change in a vascular pathway, such as an abdominal aortic aneurysm, using a simple configuration that can be implemented during a health checkup or the like.

To achieve the aforementioned object, according to one aspect of the invention, a measurement apparatus includes: a first measurement unit, worn on a first measurement area of a measurement subject that corresponds to a body surface at an area to which blood travels from the heart through a first vascular pathway, for measuring a first pulse wave signal; a second measurement unit, worn on a second measurement area of the measurement subject that corresponds to a body surface at an area to which blood travels from the heart through a second vascular pathway, for measuring a second pulse wave signal; an extraction unit for extracting a predetermined frequency component from the first pulse wave signal and the second pulse wave signal; a first propagation velocity evaluation unit for calculating, based on the extracted frequency component, a first pulse wave velocity in a first frequency that has been shown in advance not to be influenced by a predetermined pathologic change in the second vascular pathway; a second propagation velocity evaluation unit for calculating, based on the first pulse wave signal and the second pulse wave signal, a second pulse wave velocity using a different method than the first propagation velocity evaluation unit; and an output unit for outputting a degree to which the first pulse wave velocity and the second pulse wave velocity match.

Preferably, the first propagation velocity evaluation unit calculates the first pulse wave velocity based on a phase difference between the first pulse wave signal and the second pulse wave signal at the first frequency, the first frequency, and a difference in a distance from the heart to the first measurement area and a distance from the heart to the second measurement area.

Preferably, the second propagation velocity evaluation unit calculates the second pulse wave velocity based on a propagation time difference obtained by comparing a predetermined position in a pulse wave shape obtained by rendering the first pulse wave signal on a time axis with a predetermined position in a pulse wave shape obtained by rendering the second pulse wave signal on a time axis, and based on a distance from the heart to the first measurement area and a distance from the heart to the second measurement area.

Preferably, based on the frequency component extracted from the first pulse wave signal and the second pulse wave signal, the second propagation velocity evaluation unit calculates the second pulse wave velocity based on a phase difference in pulse waves in a second frequency that has been shown in advance to be influenced by the predetermined pathologic change in the second vascular pathway.

According to another aspect of the invention, a measurement method includes: a step of measuring a first pulse wave signal at a first measurement area of a measurement subject that corresponds to a body surface at an area to which blood travels from the heart through a first vascular pathway; a step of measuring a second pulse wave signal at a second measurement area of the measurement subject that corresponds to a body surface at an area to which blood travels from the heart through a second vascular pathway; a step of extracting a predetermined frequency component from the first pulse wave signal and the second pulse wave signal; a step of calculating, based on the extracted frequency component, a first pulse wave velocity in a first frequency that has been shown in advance not to be influenced by a predetermined pathologic change in the second vascular pathway; a step of calculating, based on the first pulse wave signal and the second pulse wave signal, a second pulse wave velocity using a different method than the step of calculating the first pulse wave velocity; and a step of outputting a degree to which the first pulse wave velocity and the second pulse wave velocity match.

According to this invention, the likelihood of a predetermined pathologic change in a vascular pathway, such as an abdominal aortic aneurysm, can be evaluated accurately, using a simple configuration.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
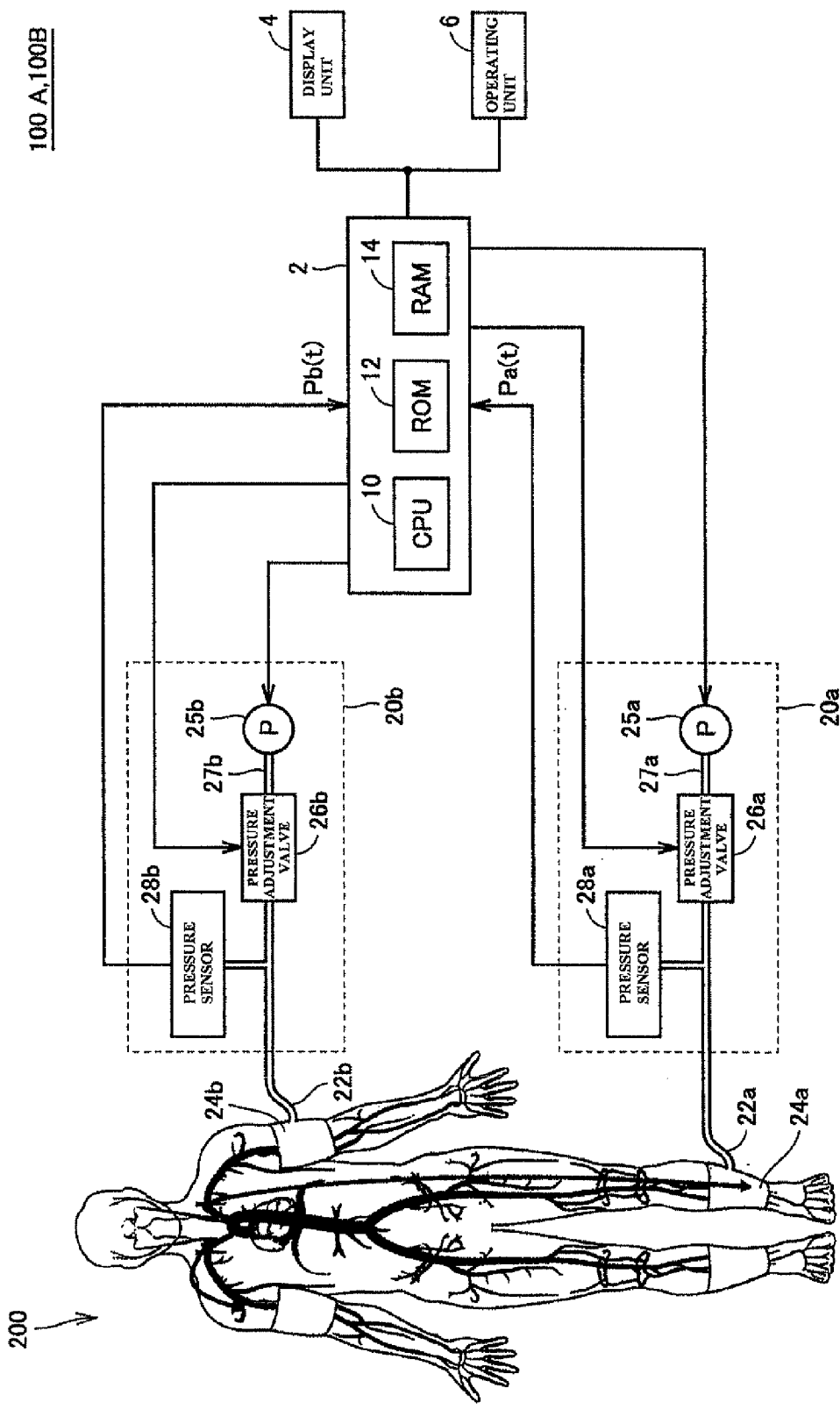
FIG. 1 is a general block diagram illustrating a measurement apparatus according to a first embodiment.

Hereinafter, embodiments of the present invention will be described with reference to the drawings. In the following descriptions, identical reference numerals are added to identical components or constituent elements. The names and functions thereof are also the same.

Apparatus Configuration

FIG. 1 is a general block diagram illustrating a measurement apparatus 100A according to a first embodiment.

As shown in FIG. 1, the measurement apparatus 100A includes a control unit 2, a display unit 4, an operating unit 6, and measurement units 20a and 20b.

The control unit 2 is a unit that controls the measurement apparatus 100A as a whole, and is typically configured of a computer including a CPU (central processing unit) 10, a ROM (read-only memory) 12, and a RAM (random access memory) 14.

The CPU 10 corresponds to a central processing unit that reads out programs stored in advance in the ROM 12 and executes those programs while using the RAM 14 as a working memory.

The display unit 4 and the operating unit 6 are connected to the control unit 2. The display unit 4 prompts a user to input various types of settings, displays results of computations performed by the control unit 2, and so on. In response to this, the user operates the operating unit 6 while confirming the content displayed in the display unit 4, and performs desired setting inputs, operations, and so on. Note that the display unit 4 is configured of, for example, an LED (light-emitting diode) display, an LCD (liquid-crystal display), or the like.

More specifically, the control unit 2 provides a measurement instruction to the measurement units 20a and 20b, receives measurement signals Pa(t) and Pb(t) obtained through measurement in response to the measurement instruction, and based on the measurement signals Pa(t) and Pb(t), executes a method for evaluating whether or not a predetermined pathologic change is present according to the present embodiment.

The measurement units 20a and 20b measure time waveforms of pulse waves at predetermined measurement areas of a measurement subject 200 by increasing the internal pressure (called "cuff pressure" hereinafter) of pressure cuffs (air bladders) 24a and 24b worn on the respective measurement areas. Note that, as will be discussed later, the control unit 2 calculates phase difference characteristics in actual measurements based on phase differences between respective frequency components in the measurement signal Pa(t) and the measurement signal Pb(t), and thus the control unit 2 provides the measurement instructions simultaneously so that the measurement units 20a and 20h can obtain the measurement signals in synchronization.

To be more specific, for example, the pressure cuffs 24a and 24b are worn on an ankle area and an upper arm area, respectively, of the measurement subject 200, and are inflated by air supplied from the measurement units 20a and 20b via tubes 22a and 22b, respectively. Due to this inflation, the measurement areas corresponding to the pressure cuffs 24a and 24b are pressurized, and pressure changes resulting from pulse waves at the measurement areas are transmitted to the measurement units 20a and 20b via the tubes 22a and 22b. The measurement units 20a and 20b measure time waveforms of the pulse waves at the measurement areas by detecting these transmitted pressure changes. Note that it is preferable for computational processes to be carried out on a predetermined frequency component (for example, 0-20 Hz) of the measurement signals Pa(t) and Pb(t), and thus it is preferable for a measurement cycle (sampling cycle) of the measurement signals Pa(t) and Pb(t) to be shorter than a time interval based on that frequency component (for example, 25 ms).

In order to execute such measurement processes, the measurement unit 20a includes a pressure sensor 28a, a pressure adjustment valve 26a, a pressure pump 25a, and a tube 27a. The pressure sensor 28a is a detection section for detecting pressure fluctuations transmitted via the tube 22a, and, for example, includes multiple sensor elements arranged at predetermined intervals on a semiconductor chip configured of single-crystal silicon or the like. The pressure adjustment valve 26a is provided between the pressure pump 25a and the pressure cuff 24a, and maintains a pressure used to inflate the pressure cuff 24a during measurement in a predetermined range. The pressure pump 25a operates in response to the measurement instruction from the control unit 2, and supplies inflation air for inflating the pressure cuff 24a.

Likewise, the measurement unit 20b includes a pressure sensor 28b, a pressure adjustment valve 26b, a pressure pump 25b, and a tube 27b. The configurations of the respective units are the same as those of the measurement unit 20a.

Although the present embodiment describes a configuration in which pressure changes caused by pulse waves, which serve as an example of a biological signal, are measured using a pressure cuff, it should be noted that, for example, a minute constant current may be applied to measurement areas of the measurement subject 200 and voltage changes resulting from changes in the impedance produced in accordance with the travel of pulse waves (that is, a body impedance) may be measured instead.

Function Block Diagram

By the CPU 10 executing computational processes in accordance with programs stored in the ROM 12 in advance, the control unit 2 uses two types of methods to calculate differences in the velocities of pulse waves at the respective measurement areas on which the pressure cuffs 24a and 24b are worn, and evaluates the likelihood of a predetermined pathologic change in a vascular pathway based on a comparison between those velocities. Functional blocks in the control unit 2 for implementing such processing operations will now be described.

Figure 2:
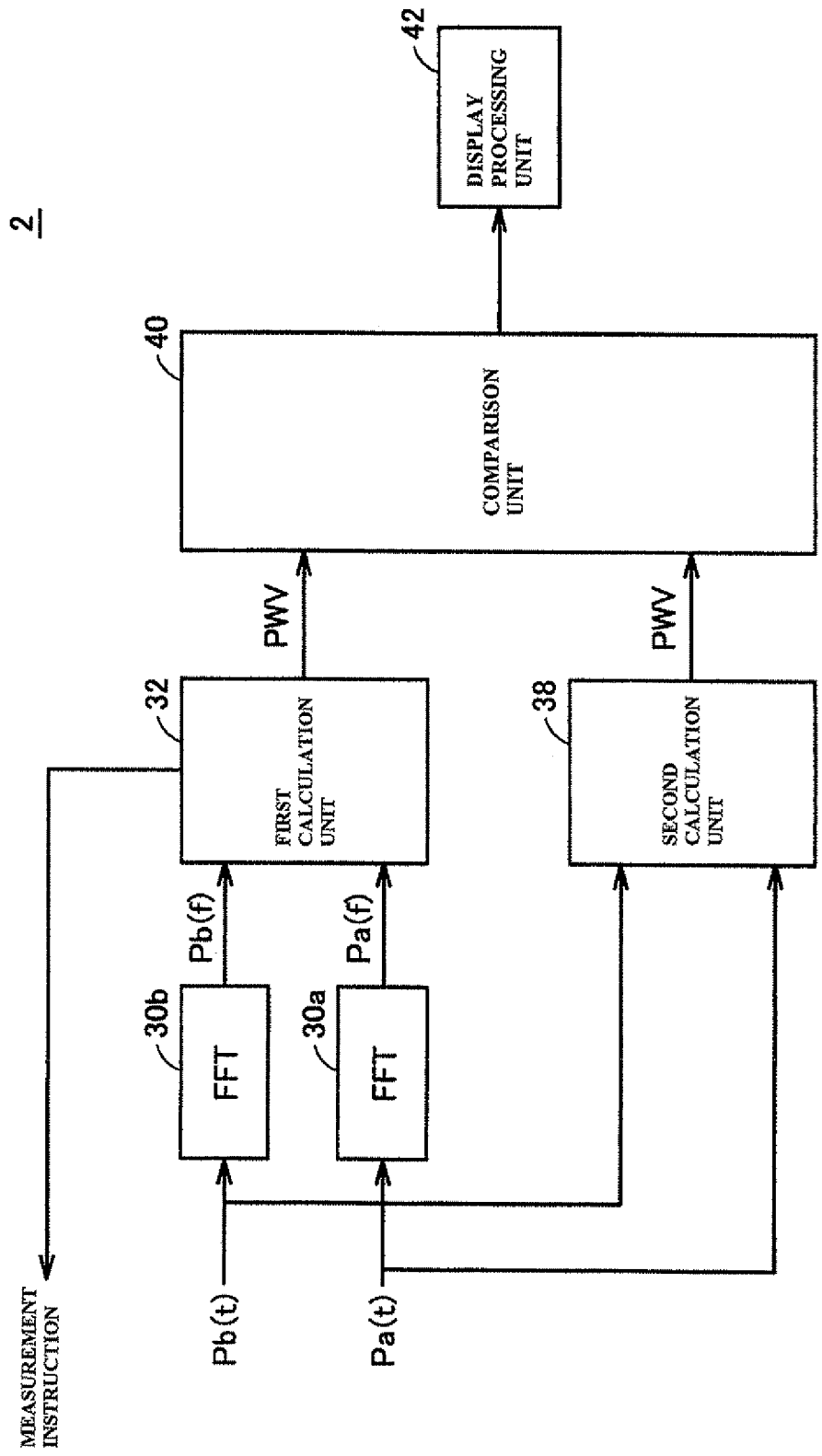
FIG. 2 is a function block diagram schematically illustrating functions executed by a control unit of the measurement apparatus according to the first embodiment.

FIG. 2 is a function block diagram schematically illustrating functions executed by the control unit 2 of the measurement apparatus 100A.

As shown in FIG. 2, the control unit 2 implements frequency transform units (FFT) 30a and 30b, a first calculation unit 32, a second calculation unit 38, a comparison unit 40, and a display processing unit 42.

The frequency transform units 30a and 30b are frequency transform units that receive the measurement signals Pa(t) and Pb(t), which are time waveforms, over a predetermined period, and transform the received measurement signals Pa(t) and Pb(t) into frequency domain functions. Generally, the frequency transform units 30a and 30b execute the frequency transforms using fast Fourier transforms (FFT).

Note that this transform is not limited to a fast Fourier transform, and may use any logic as long as it converts a time domain function into a frequency domain function, such as a Fourier series.

The frequency transform unit 30a calculates a phase characteristic Pa(f) indicating a phase for each frequency component in the measurement signal Pa(t), and outputs the calculated phase characteristic Pa(f) to the first calculation unit 32. Likewise, the frequency transform unit 30b calculates a phase characteristic Pb(f) indicating a phase for each frequency component in the measurement signal Pb(t), and outputs the calculated phase characteristic Pb(f) to the first calculation unit 32.

The first calculation unit 32 provides the measurement instructions to the measurement units 20a and 20b in response to operations performed by the user through the operating unit 6 (FIG. 1) or the like. After providing these measurement instructions, the first calculation unit 32 receives the phase characteristic Pa(f) and phase characteristic Pb(f) outputted from the frequency transform units 30a and 30b, and calculates a pulse wave velocity (PWV) based on the phase differences at each frequency component between the phase characteristics.

The second calculation unit 38 calculates the pulse wave velocity (PWV) through a different method than the first calculation unit 32. Specifically, the second calculation unit 38 receives the measurement signals Pa(t) and Pb(t) over a predetermined period, and calculates the pulse wave velocity (PWV) using the received measurement signals Pa(t) and Pb(t).

The calculation methods employed by the respective calculation units will be described.

Calculation of Pulse Wave Velocity by First Calculation Unit 32

The first calculation unit 32 compares the values of the phase characteristics Pa(f) and Pb(f) for each frequency component and calculates a phase difference therebetween.

First, using a model in which a blood vessel is taken as a thin-walled tube with minute uniform deformations, the flow within the blood vessel is a nonviscous fluid layer flow, and no reflected waves are assumed to be present, the relationship between a pulse wave speed Cp and the Young's modulus E of the blood vessel wall is expressed as indicated in Formula (1), which is also called the Moens-Korteweg equation. Note that the pulse wave speed Cp indicates the speed at which blood pressure changes resulting from the heartbeat are transmitted through the blood vessel.

$$C_P = \sqrt{\frac{Eh}{2r\rho}} \quad (1)$$

(where h represents the vessel wall thickness, r represents the inner diameter of the vessel, and ρ represents the density of the blood)

From Formula (1), it can be seen that the pulse wave speed Cp will increase when the blood vessels are harder, the inner space thereof is narrower, or the blood vessel walls are thicker.

Figure 3:
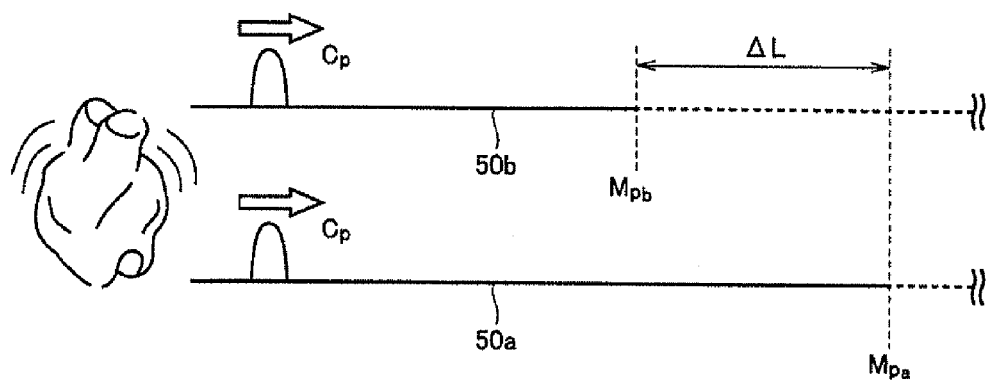
FIG. 3 is a schematic diagram illustrating pulse waves in a uniform tract.

FIG. 3 is a schematic diagram illustrating pulse waves in a uniform tract.

As shown in FIG. 3, it is assumed that no reflected waves are present and the pulse wave speed Cp is a constant that does not depend on the frequency provided in Formula (1). Such being the case, a pulse wave phase delay φ at a measurement area Mpa relative to a measurement area Mpb is expressed through Formula (2).

$$\phi = -360 \times \frac{\Delta L}{\lambda} \quad (2)$$

(where L represents the pathway difference between measurement times)

Rewriting Formula (2) using the pulse wave speed Cp and a frequency f results in Formula (3).

$$\phi = -360 \times \frac{\Delta L}{c_p} f \quad (3)$$

From Formula (2), it can be seen that a phase diagram (phase difference characteristics) between the measurement area Mpa and the measurement area Mpb is a direct function of the frequency f, and the slope thereof is a value that is based on the pulse wave speed Cp. Furthermore, Formula (4) can be obtained using Formulas (1) and (3).

$$\phi = -360 \times \sqrt{\frac{2r\rho\Delta L^2}{Eh}} f \quad (4)$$

From Formula (4), it can be seen that the slope of the phase diagram becomes gentler the greater the Young's modulus E of the blood vessel wall is.

Here, it is known that the phase of a low-frequency band is affected by the presence of a predetermined pathologic change such as an arterial aneurysm in a vascular pathway. Specifically, 0 Hz to 10 Hz is assumed as a low-frequency band. Accordingly, the pulse wave velocity (PWV) calculated by the first calculation unit 32 through the following method can be called a pulse wave velocity (PWV) resulting in a case where it is assumed that there is no influence from a predetermined pathologic change in a vascular pathway.

The first calculation unit 32 calculates a slope gexp of a phase line using high-frequency components of the measurement signal Pa(t) and the measurement signal Pb(t), which is a frequency band that has been shown not to be influenced by a predetermined pathologic change in a vascular pathway. As a specific example, the slope gexp (deg/Hz) of the phase line is calculated using the phase characteristics Pa(f) and Pb(f) in a 10 Hz to 20 Hz range.

As described earlier, the phase difference in the values of the phase characteristics Pa(f) and Pb(f) can be approximated as a direct function of the frequency components, and thus the slope gexp (deg/Hz) of this approximated direct function (phase line) can be defined as slope gexp tan(ϕexp), using a declination ϕ calculated as declination ϕexp=∠phase characteristic Pa(f)/phase characteristic Pb(f).

When the phase differences between the measurement signal Pa(t) and the measurement signal Pb(t) at each frequency component are plotted, the phase diagram has discontinuous points with a ±180° boundary. This indicates that a phase difference greater than or equal to one cycle (360°) is present in frequency components greater than or equal to a predetermined frequency. Accordingly, the first calculation unit 32 calculates an actual phase difference characteristic after correcting the discontinuous points in the phase diagram with a unit(n×360° equivalent to one or two cycles.

Then, the first calculation unit 32 compares the phase characteristic Pa(f) obtained by performing a frequency transform on the measurement signal Pa(t) with the phase characteristic Pb(f) obtained by performing a frequency transform on the measurement signal Pb(t), and plots phase differences Ai that correspond to frequencies fi on the phase diagram. Note that the frequency fi is the ith frequency component, counting from the low-frequency side. By correcting the discontinuous points in the phase diagram as described above, the phase diagram that is plotted becomes continuous. The first calculation unit 32 then calculates a regression line using the phase difference in the stated low-frequency band (0 Hz to 10 Hz) for the phase differences Ai plotted on the phase diagram. The slope of the regression line corresponds to the slope gexp indicated in FIG. 2.

The first calculation unit 32 stores, in advance, the distances from the heart to the vascular pathways in the measurement areas on which the pressure cuffs 24a and 24b are worn, or a difference ΔL between those distances. The first calculation unit 32 then calculates the pulse wave velocity (PWV) by dividing the distance difference ΔL by a propagation time difference Td obtained as the slope gexp of the phase line. The first calculation unit 32 outputs the calculated pulse wave velocity (PWV) to the comparison unit 40.

Calculation of Pulse Wave Velocity by Second Calculation Unit 38

The second calculation unit 38 receives the measurement signals Pa(t) and Pb(t) over a predetermined period, and obtains an appearance time difference of a predetermined position of a pulse waveform, obtained by rendering the received measurement signals Pa(t) and Pb(t) on respective time axes, as the propagation time difference Td.

Figure 4:
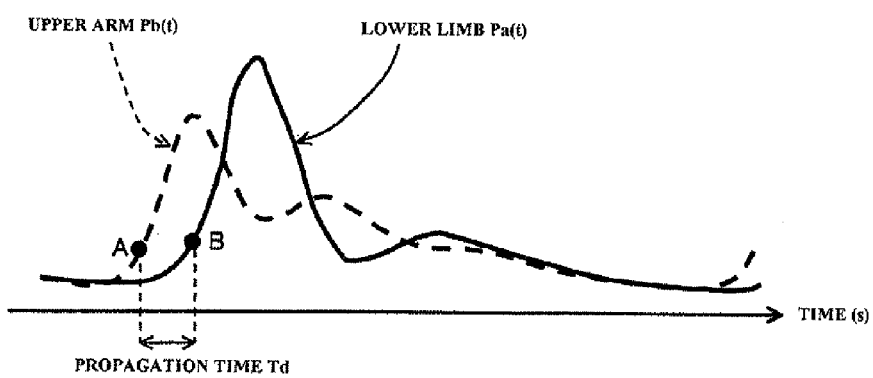
FIG. 4 is a schematic diagram illustrating pulse waveforms obtained by rendering measurement signals Pa(t) and Pb(t) from respective measurement areas along respective time axes.

FIG. 4 is a schematic diagram illustrating pulse waveforms obtained by rendering the measurement signals Pa(t) and Pb(t) along respective time axes. For example, the position of the pulse waveform at the point in time where the pulse wave amplitude has risen from a rising position ⅕ the difference between a minimum value and a maximum value in a single pulse in the pulse waveform can be employed as the predetermined position of the pulse waveform. This is because the rise position is easily susceptible to the influence of noise and the like.

In the example shown in FIG. 4, the second calculation unit 38 obtains, as the propagation time difference Td, the appearance time difference between a point A and a point B, which are the positions of the pulse waveforms at the point in time where the pulse wave amplitude has risen from a rising position ⅕ the difference between a minimum value and a maximum value in a single pulse in the pulse waveform resulting from the measurement signals Pa(t) and Pb(t), respectively.

Note that in the case where the second calculation unit 38 includes a band pass filter that allows only a predetermined frequency to pass, the appearance time difference of that frequency in the pulse waveform can be obtained as the propagation time difference Td instead of the appearance time difference at the predetermined position.

The second calculation unit 38 stores, in advance, the distances in the vascular pathways from the heart to the measurement areas on which the pressure cuffs 24a and 24b are worn, or the difference ΔL between those distances, and calculates the pulse wave velocity by dividing the distance difference ΔL by the propagation time difference Td. The second calculation unit 38 outputs the calculated pulse wave velocity to the comparison unit 40.

Note that the second calculation unit 38 does not use only a frequency band that has been shown, in advance, not to be influenced by a predetermined pathologic change in a vascular pathway from the pulse waveform obtained by rendering the measurement signals Pa(t) and Pb(t) on respective time axes. Accordingly, the pulse wave velocity (PWV) calculated by the second calculation unit 38 through the aforementioned method can be called a pulse wave velocity (PWV) that is likely influenced by a predetermined pathologic change in a vascular pathway, assuming such a pathologic change is present.

The comparison unit 40 compares the pulse wave velocity (PWV) calculated by the first calculation unit 32 through the aforementioned method with the pulse wave velocity (PWV) calculated by the second calculation unit 38 through the aforementioned method. In the case where, as a result, the ratio of the pulse wave velocity (PWV) calculated by the first calculation unit 32 to the pulse wave velocity (PWV) calculated by the second calculation unit 38 is within a threshold stored in advance, it is assumed that the pulse wave velocities (PWV) calculated through these two methods are equal, and an evaluation result indicating that a predetermined pathologic change, such as an arterial aneurysm, is not present in a vascular pathway is outputted to the display processing unit 42. On the other hand, in the case where the ratio of the pulse wave velocities (PWV) is greater than the threshold stored in advance, it is assumed that there is a difference equivalent to a predetermined amount or greater in the pulse wave velocities (PWV) calculated through the two methods, and an evaluation result indicating that a predetermined pathologic change, such as an arterial aneurysm, may be present in a vascular pathway is outputted to the display processing unit 42.

Note that the comparison unit 40 may use a difference, instead of a ratio, when comparing the pulse wave velocities. In other words, a similar evaluation may be carried out based on whether the difference is greater or less than a threshold.

The display processing unit 42 executes a process for displaying the evaluation result from the comparison unit 40 in the display unit 4. In addition, the calculated pulse wave velocities (PWV), the aforementioned ratio, or the like may also be displayed in addition to the evaluation result.

Flowchart

Figure 5:
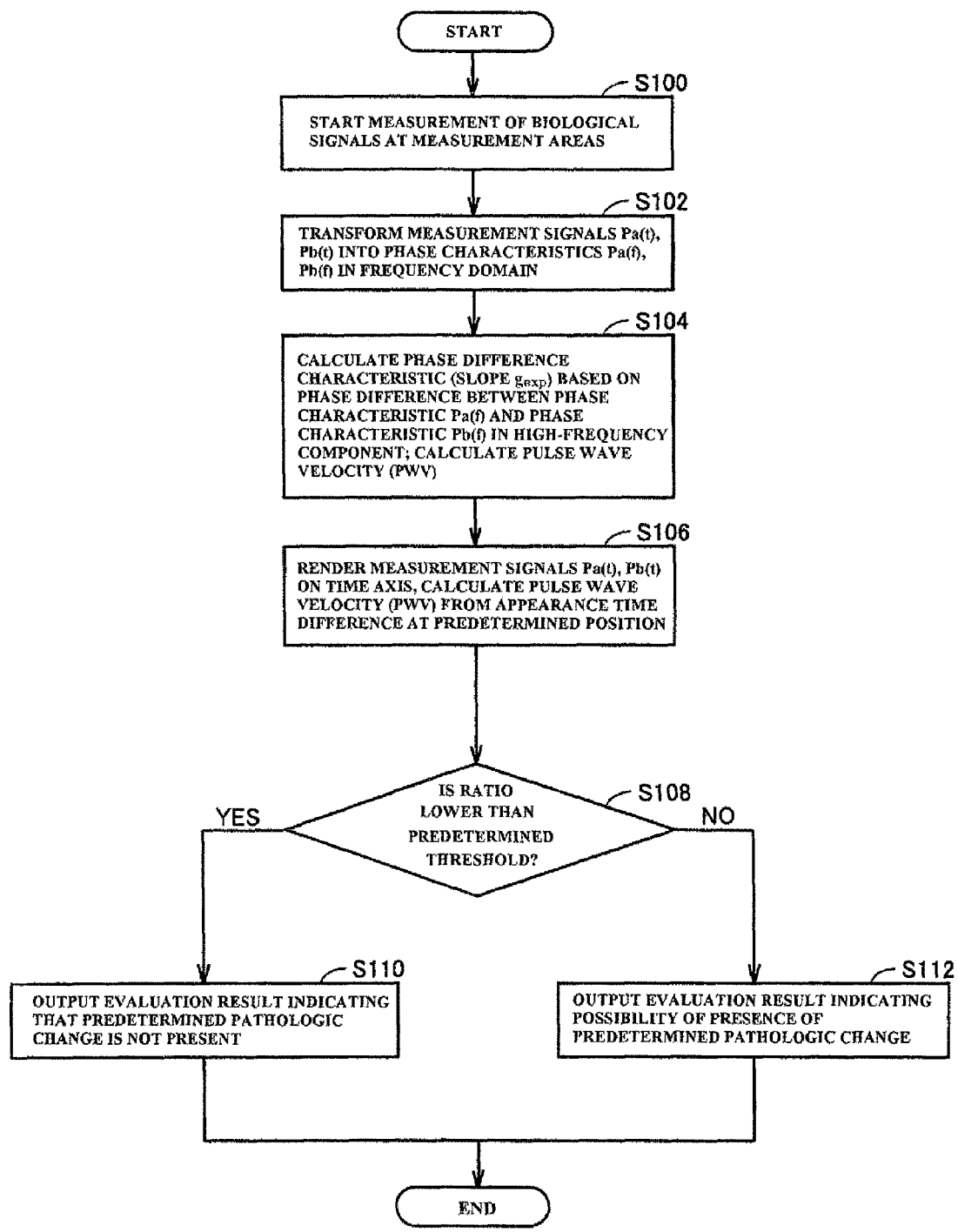
FIG. 5 is a flowchart illustrating a procedure for a process executed by the measurement apparatus according to the first embodiment.

FIG. 5 is a flowchart illustrating a procedure for a process executed by the measurement apparatus 100A according to the first embodiment. The various processes indicated in the flowchart shown in FIG. 5 are implemented by the various functions shown in FIG. 2, by the CPU 10 of the control unit 2 reading out programs stored in advance in the ROM 12, expanding those programs in the RAM 14, and executing the programs.

As shown in FIG. 5, the CPU 10 provides the measurement instruction to the measurement units 20a and 20b in response to the user operating the operating unit 6 or the like, and the measurement units 20a and 20b commence the measurement of biological signals at the predetermined measurement areas of the measurement subject 200 (step S100).

Next, the CPU 10 converts the measurement signals Pa(t) and Pb(t), which are time waveforms measured by the measurement units 20a and 20b, into the phase characteristics Pa(f) and Pb(f) in a frequency domain (step S102). Then, the CPU 10 calculates the phase difference characteristic (slope gexp) based on the phase difference in the high-frequency components (10 Hz to 20 Hz) between the phase characteristic Pa(f) and the phase characteristic Pb(f), and calculates the pulse wave velocities (PWV) by dividing the pre-stored distance differences ΔL in the vascular pathways from the heart to the measurement areas on which the pressure cuffs 24a and 24b are worn by the propagation time difference Td obtained as the slope gexp (step S104).

Meanwhile, the CPU 10 obtains, as the propagation time difference Td, the appearance time difference, at a predetermined position, of the respective pulse waveforms obtained by rendering the measurement signals Pa(t) and Pb(t), which are time waveforms measured by the measurement units 20a and 20b, on respective time axes. Then, the CPU 10 calculates the pulse wave velocities (PWV) by dividing the distance differences ΔL in the vascular pathways from the heart to the measurement areas on which the pressure cuffs 24a and 24b are worn, which are stored in advance, by the propagation time difference Td (step S106).

Note that the order of the processes from steps S102 to S104 and the process of step S106 need not follow the stated order, and may be executed in reverse, or executed in parallel.

Thereafter, the CPU 10 compares the pulse wave velocities (PWV) calculated in step S104 with the pulse wave velocities (PWV) calculated in step S106, and determines whether or not the ratio between the two is less than a predetermined threshold (step S108).

In the case where the ratio is less than the predetermined threshold (YES in step S108), the CPU 10 assumes that a predetermined pathologic change, such as an arterial aneurysm, is not present in a vascular pathway from the heart to the measurement areas on which the pressure cuffs 24a and 24b are worn, and outputs an evaluation result indicating such to the display unit 4 (step S110).

On the other hand, in the case where the ratio is greater than the predetermined threshold (NO in step S108), the CPU 10 assumes that a predetermined pathologic change, such as an arterial aneurysm, may be present in a vascular pathway from the heart to the measurement areas on which the pressure cuffs 24a and 24b are worn, and outputs an evaluation result indicating such to the display unit 4 (step S112). After this, the measurement process ends.

According to the first embodiment of this invention, it is possible to easily and accurately evaluate whether or not a predetermined pathologic change, such as an arterial aneurysm, is present in a vascular pathway leading to the measurement areas, using the values obtained from cuff pressure changes in the pressure cuffs 24a and 24b.

Second Embodiment

Apparatus Configuration

The apparatus configuration of a measurement apparatus 100B according to a second embodiment is the same as the configuration of the measurement apparatus 100A illustrated in FIG. 1.

Function Block Diagram

Figure 6:
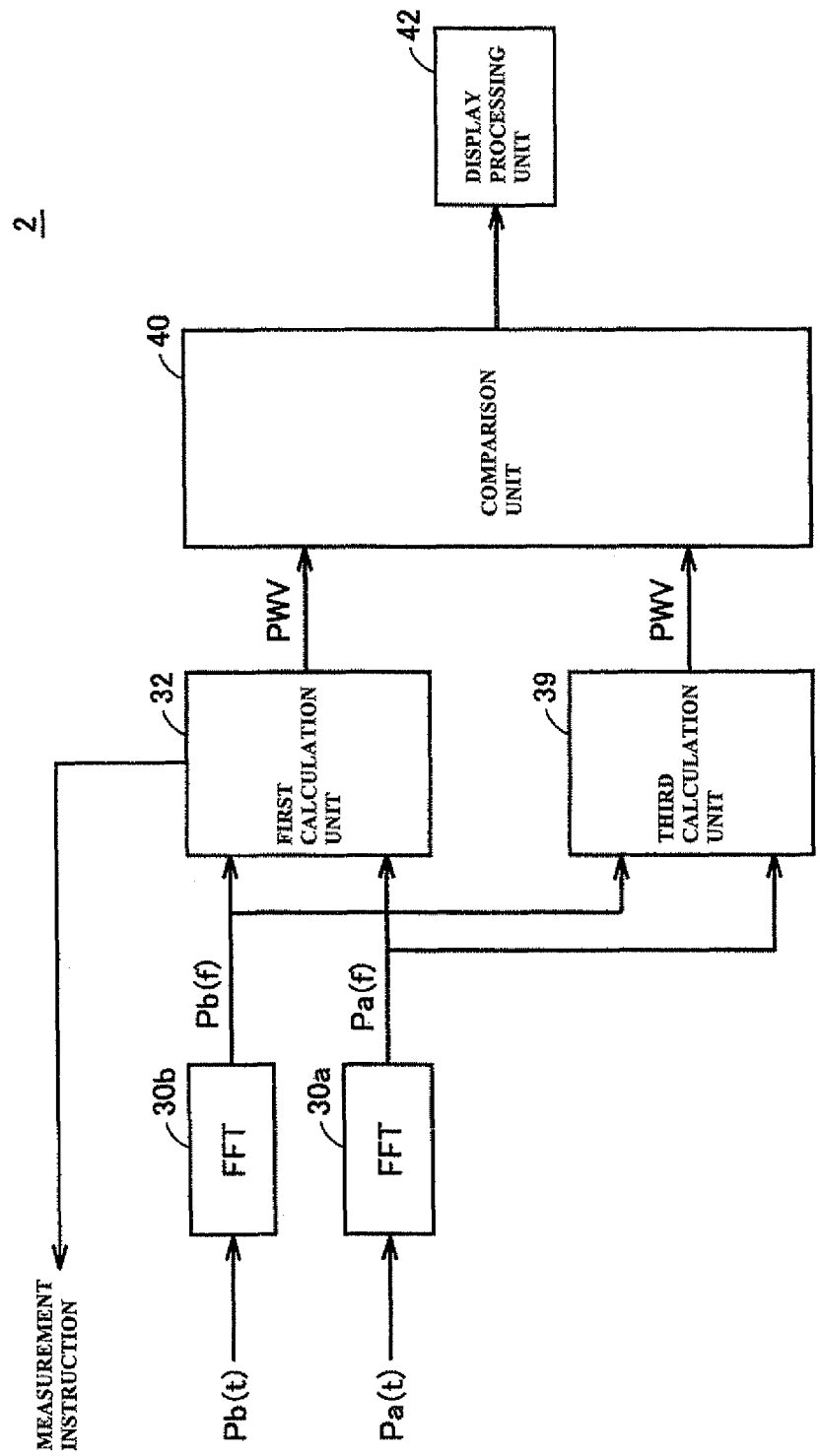
FIG. 6 is a function block diagram schematically illustrating functions executed by a control unit of the measurement apparatus according to a second embodiment.

FIG. 6 is a function block diagram schematically illustrating functions executed by the control unit 2 of the measurement apparatus 100B.

As shown in FIG. 6, the control unit 2 implements the frequency transform units (PFT) 30a and 30b, the first calculation unit 32, a third calculation unit 39, the comparison unit 40, and the display processing unit 42. In other words, the control unit 2 of the measurement apparatus 100B implements the third calculation unit 39 instead of the second calculation unit 38 implemented by the control unit 2 of the measurement apparatus 100A; the other elements are the same as in the control unit 2 of the measurement apparatus 100A. The differences will be described hereinafter.

Calculation of Pulse Wave Velocity by Third Calculation Unit 39

With the control unit 2 of the measurement apparatus 100B, the frequency transform unit 30a calculates the phase characteristic Pa(f) indicating a phase for each frequency component in the measurement signal Pa(t), and outputs the calculated phase characteristic Pa(f) to the first calculation unit 32 and the third calculation unit 39. Likewise, the frequency transform unit 30b calculates the phase characteristic Pb(f) indicating a phase for each frequency component in the measurement signal Pb(t), and outputs the calculated phase characteristic Pb(f) to the first calculation unit 32 and the third calculation unit 39.

The third calculation unit 39 calculates the pulse wave velocity (PWV) through a different method than the first calculation unit 32. Specifically, the third calculation unit 39 compares the values of the phase characteristics Pa(f) and Pb(f) for each frequency component in a frequency band that has been shown, in advance, to be influenced by a predetermined pathologic change in a vascular pathway when such a pathologic change is present, and calculates a phase difference therebetween. In other words, the third calculation unit 39 calculates a slope gexp of a phase line using low-frequency components of the measurement signal Pa(t) and the measurement signal Pb(t), which is a frequency band that has been shown to be influenced by a predetermined pathologic change in a vascular pathway when such a pathologic change is present. As a specific example, the slope gexp of the phase line is calculated using the phase characteristics Pa(f) and Pb(f) in a 0 Hz to 10 Hz range. Accordingly, the pulse wave velocity (PWV) calculated by the third calculation unit 39 can be called a pulse wave velocity (PWV) that is likely influenced by a predetermined pathologic change in a vascular pathway, assuming such a pathologic change is present.

Flowchart

Figure 7:
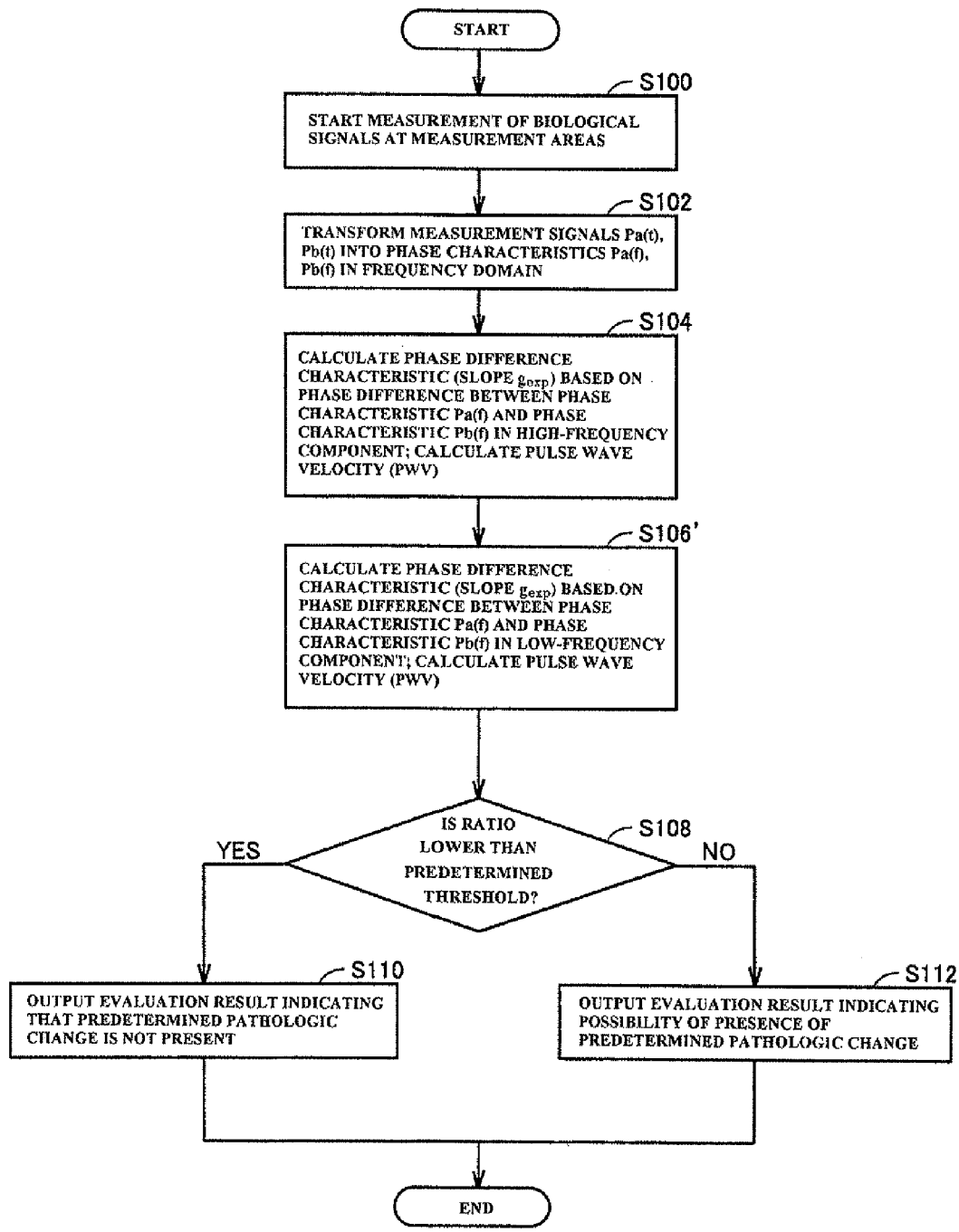
FIG. 7 is a flowchart illustrating a procedure for a process executed by the measurement apparatus according to the second embodiment.

FIG. 7 is a flowchart illustrating a procedure for a process executed by the measurement apparatus 100B according to the second embodiment. The various processes indicated in the flowchart shown in FIG. 7 are implemented by the various functions shown in FIG. 6, by the CPU 10 of the control unit 2 reading out programs stored in advance in the ROM 12, expanding those programs in the RAM 14, and executing the programs.

In FIG. 7, processes to which the same step numbers as those in the flowchart in FIG. 5 have been given are the same processes as those in the flowchart in FIG. 5. Accordingly, after the measurement units 20a and 20b commence the measurement of biological signals at the predetermined measurement areas of the measurement subject 200 in step S100, in steps S102 to S104, the CPU 10 calculates the propagation time difference Td based on the phase difference in the high-frequency component (10 Hz to 20 Hz) of the phase characteristic Pa(f) and the phase characteristic Pb(f), and calculates the pulse wave velocities (PWV) by dividing the pre-stored differences ΔL in the distances in the vascular pathways from the heart to the measurement areas on which the pressure cuffs 24a and 24b are worn by the propagation time difference Td obtained as the slope gexp.

In the second embodiment, the CPU 10 calculates the propagation time difference Td based on the phase difference in the low-frequency component (0 Hz to 10 Hz) between the phase characteristic Pa(f) and the phase characteristic Pb(f), and calculates the pulse wave velocities (PWV) by dividing the pre-stored differences ΔL in the distances in the vascular pathways from the heart to the measurement areas on which the pressure cuffs 24a and 24b are worn by the propagation time difference Td obtained as the slope gexp (step S106').

Note that the order of the processes from steps S102 to S104 and the process of step S106' need not follow the stated order, and may be executed in reverse, or executed in parallel.

Thereafter, the CPU 10 compares the pulse wave velocities (PWV) calculated in step S104 with the pulse wave velocities (PWV) calculated in step S106', and in the case where the ratio is less than a predetermined threshold (YES in step S108), the CPU 10 assumes that a predetermined pathologic change, such as an arterial aneurysm, is not present in a vascular pathway from the heart to the measurement areas on which the pressure cuffs 24a and 24b are worn, and outputs an evaluation result indicating such to the display unit 4 (step S110), whereas in the case where the ratio is greater than the predetermined threshold (NO in step S108), the CPU 10 assumes that a predetermined pathologic change, such as an arterial aneurysm, may be present and outputs an evaluation result indicating such to the display unit 4 (step S112). After this, the measurement process ends.

According to the second embodiment of this invention as well, it is possible to easily and accurately evaluate whether or not a predetermined pathologic change, such as an arterial aneurysm, is present in a vascular pathway leading to the measurement areas, using the values obtained from cuff pressure changes in the pressure cuffs 24a and 24b.

Verification of Measurement Apparatus 100A through Simulation

The inventors carried out simulations using models, and verified the evaluation results of the measurement apparatus 100A.

Circulatory System Model

In this verification, a circulatory system model in which the blood vessels within a body were broken up into multiple segments and modeled was used. What is known as the "Avolio model", described in Reference Document 1, "Avolio, A. P, Multi-branched Model of Human Arterial System, 1980, Med. & Biol. Engng. & Comp., 18, 796", is known as a representative example of such a circulatory system model, and the Avolio model was employed as the circulatory system model in this verification as well.

In the Avolio model, the arteries of the entire body are divided into 128 blood vessel elements (segments), and geometric values that represent the respective segments are defined. In the Avolio model, a length, radius, vessel wall thickness, Young's modulus, and so on associated with the respective segments are included as geometric values. Note that Young's modulus is, in the Avolio model, a preliminary base value, and in the verification, values from two to five times the Young's modulus base value were used to represent individual differences.

This circulatory system model classifies various blood vessels that make up a body into multiple segments, and models the blood vessels belonging to at least one segment among the multiple segments. Generally speaking, the blood vessels are divided based on the magnitude of the vessel radius, into the aorta, medium arteries (ϕ3.2 mm or greater), small arteries (ϕ0.5 mm or greater), arteriolae (ϕ0.03 mm or greater), capillaries, and so on. The Avolio model models the blood vessels that, from among those segments, are segmented as the aorta and medium arteries.

Note that the method for segmenting the blood vessels is not limited to the magnitude of the vessel radius, and the segmentation may be carried out based on another index.

Figure 8:
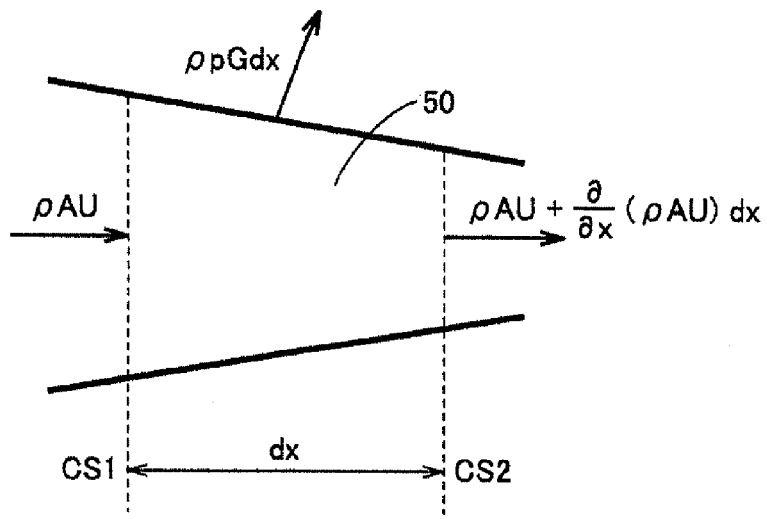
FIG. 8 is a diagram illustrating a one-dimensional flow model for blood in a blood vessel.

FIG. 8 is a diagram illustrating a one-dimensional flow model for blood in a blood vessel.

Generally, blood has a sufficiently high volume elasticity compared to blood vessels, and thus a blood vessel can be thought of as a circular elastic tube, and blood can be thought of as an incompressible fluid. The governing equation for a one-dimensional flow in such an elastic tube can be derived as follows.

The conservation of the mass regarding a control volume 50 between cross-sections CS1-CS2 of the one-dimensional flow model will be considered, with reference to FIG. 8. Assuming that the interior surface area of the cross-section CS1 is A(=πri2), the density of the fluid (blood) is β, the pressure is p, and the cross-section average flow velocity is U, and that the volume of the fluid that flows out to a branched blood vessel located between the cross-sections CS1-CS2 in a unit of time is G for every unit of length and unit of pressure, Formula (5) holds true under the law of conservation of mass. Here, with an incompressible fluid, the density ρ is constant, and thus Formula (5) can be simplified as Formula (6).

$$\frac{\partial(\rho A)}{\partial t} + \frac{\partial(\rho A U)}{\partial x} + \rho p G = 0 \quad (5)$$

$$\frac{\partial A}{\partial t} + \frac{\partial(A U)}{\partial x} + p G = 0 \quad (6)$$

Figure 9:
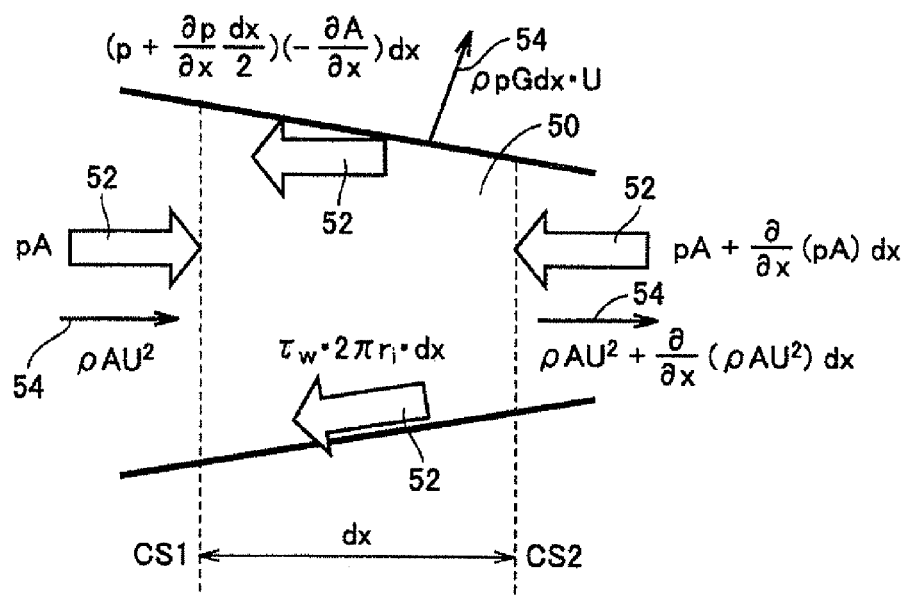
FIG. 9 is a diagram illustrating forces that act on the control volume shown in FIG. 8 and input/output movement amounts.

FIG. 9 is a diagram illustrating forces 52 that act on the control volume 50 shown in FIG. 8 and input/output movement amounts 54.

As shown in FIG. 9, a change in the movement amounts 54 in the control volume 50 per unit of time is equivalent to the inflowing net movement amount 54 and the forces 52 applied to the control volume 50, and thus Formula (7) can be arrived at by omitting the higher-order minute terms.

$$\rho\frac{\partial(AU)}{\partial t} + \rho\frac{\partial(AU^2)}{\partial x} + \rho p G U + A\frac{\partial p}{\partial x} + 2\pi r_i \tau_w = 0 \quad (7)$$

(where $\tau_w$ represents the frictional shear stress at the wall surface and $r_i$ represents the inner diameter of the blood vessel)

Arranging Formula (7) into a continuous equation results in the equation of motion indicated by Formula (8).

$$\rho\frac{\partial U}{\partial t} + \rho U\frac{\partial U}{\partial x} + \frac{\partial p}{\partial x} + \frac{2\pi r_i \tau_w}{A} = 0 \quad (8)$$

Next, in order to create a one-dimensional linear distributed parameter model for the blood vessels, Formulas (9) and (10) are obtained by omitting the nonlinear terms in Formulas (6) and (8) and replacing the variables with the pressure p and the a volume flow amount q(=AU).

$$-\frac{\partial p}{\partial x} = Rq + L\frac{\partial q}{\partial t} \quad (9)$$

$$-\frac{\partial q}{\partial x} = Gp + C\frac{\partial q}{\partial t} \quad (10)$$

Here, regarding the physical meaning of the four coefficients in Formulas (9) and (10), R represents the nonelastic resistance during blood flow, L represents the inertia of the blood that works against sudden changes when changes occur in the flow, G represents the ease at which blood flows out of the blood vessels or in the branched vessels, and C indicates the capability of blood to be stored in the blood vessels when the vessels expand/contract due to changes in pressure.

Figure 10A:
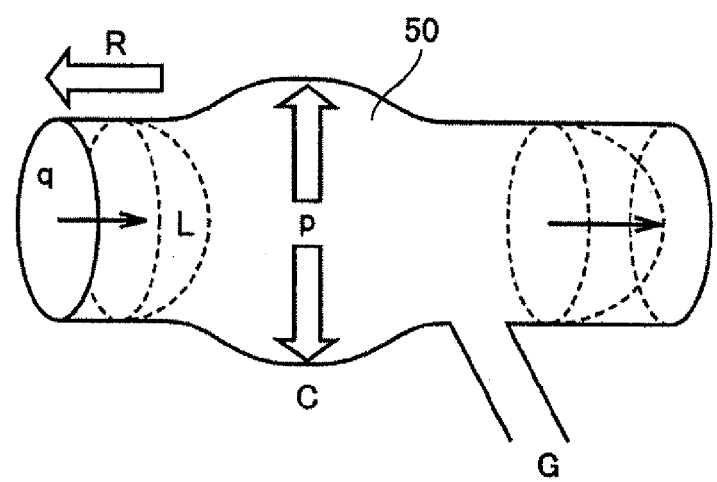
FIG. 10A is a schematic diagram illustrating a blood vessel through a one-dimensional linear distributed parameter model.
Figure 10B:
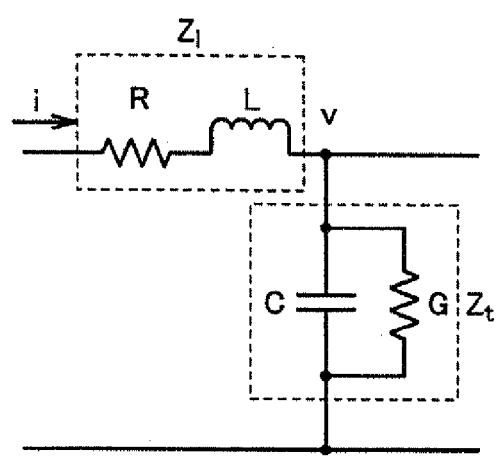
FIG. 10B is a diagram that replaces the physical model shown in FIG. 10A with an electrical analogous circuit.

FIGS. 10A and 10B are schematic diagrams illustrating a blood vessel through a one-dimensional linear distributed parameter model. FIG. 10A is a diagram corresponding to Formulas (9) and (10) and the physical model of the blood vessels. FIG. 10B is a diagram that replaces the physical model shown in FIG. 10A with an electrical analogous circuit.

In other words, Formulas (9) and (10) can be associated with a physical model such as that shown in FIG. 10A. Furthermore, the physical model can be replaced with an electrical analogous circuit (distributed constant circuit) such as that shown in FIG. 10B by replacing the pressure p with a voltage v and a flow amount v with a current i in Formulas (9) and (10). Here, R expresses a resistance, L expresses an inductance, G represents an admittance, and C represents a capacitance.

Here, looking at Formula (9), while the cardiovascular system corresponds to the equation of motion, the electrical system corresponds to Ohm's law. This means that the phenomenon in which the fluid accelerates in the cardiovascular system depending on the slope of the pressure between the cross-section CS1 and the cross-section CS2 corresponds, in the electrical system, to a phenomenon in which a difference in the potentials applied to both ends of the inductance produces a current.

Meanwhile, looking at Formula (10), while the cardiovascular system corresponds to a continuous equation (the law of conservation of mass), the electrical system corresponds to the law of conservation of charge. This means that the phenomenon in which a retained amount of the mass that does not advance from the cross-section CS1 to the cross-ssection CS2 pushes open the blood vessels and causes a rise in the pressure corresponds to a phenomenon in which a charge accumulated in the capacitor causes a rise in the voltage.

Furthermore, assuming in Formulas (9) and (10) that p=Pejwt and q=Qejwt, the relational expressions indicated in Formulas (11) and (12) can be derived.

$$-\frac{\partial P}{\partial x} = (R + j\omega L)Q = Z_l Q \quad (11)$$

$$-\frac{\partial Q}{\partial x} = (G + j\omega C)P = \frac{1}{Z_t}P \quad (12)$$

(where ω represents an angular frequency)

Hereinafter, Zl (=r+jωL) indicated in FIG. 10B and in Formula (11) will be called a "vertical impedance", whereas Zt (=(G+jωC)−1) indicated in FIG. 10B and in Formula (12) will be called a "horizontal impedance". Assuming that the amplitude value of a forward wave of the pressure when x=0 is Pf and the amplitude value of a receding wave is Pr, the general solutions of Formulas (11) and (12) result in the Formulas (13) and (14), respectively. Note a relationship of $\omega=2\pi f$ holds true between the angular frequency $\omega$ and the frequency f.

$$P = P_f e^{-\gamma x} + P_r e^{\gamma x} \tag{13}$$

$$Q = \frac{1}{Z_0}(P_f e^{-\gamma x} - P_r e^{\gamma x}) \tag{14}$$

(where $\gamma$ represents a propagation constant and $Z_0$ represents a characteristic impedance)

In addition, a propagation constant $\gamma$ is expressed as indicated by Formula (15), using an attenuation constant $\beta$ and a phase speed (pulse wave speed) Cp.

$$\gamma = \sqrt{\frac{Z_l}{Z_t}} = \beta + j\frac{\omega}{C_p} \tag{15}$$

Here, the phase speed Cp is an amount indicating the distance a pulse wave travels per unit of time, whereas the attenuation constant $\beta$ indicates that the amplitude of the pulse wave is e-$\beta$ times with each unit of distance traveled. Meanwhile, a characteristic impedance Z0 is expressed by the Formula (16), and indicates the necessary pressure for a pulse wave in a unit of volume to advance in the direction of travel.

$$Z_o = \sqrt{Z_l Z_t} \tag{16}$$

Furthermore, pressures Ps and Pe and volume flow amounts Qs and Qe at two points with a distance lse therebetween are connected by the transfer matrix indicated by Formula (17).

$$\begin{Bmatrix} P_s \\ Q_s \end{Bmatrix} = \begin{bmatrix} \cosh\gamma l_{se} & Z_0 \sinh\gamma l_{se} \\ \frac{1}{Z_0}\sinh\gamma l_{se} & \cosh\gamma l_{se} \end{bmatrix} \begin{Bmatrix} P_e \\ Q_e \end{Bmatrix} \tag{17}$$

In these verifications, the transfer matrix indicated in Formula (17) is calculated in association with each segment of the blood vessels, and the transfer functions are calculated by cascade-connecting the transfer matrices corresponding to the respective segments in accordance with the target vascular pathway. At this time, the conditions downstream from a given border are expressed through Formula (18) as an impedance Zx, which is a ratio between a pressure Px and a volume speed Qx at that border.

$$Z_x = \frac{P_x}{Q_x} \tag{18}$$

In addition, a reflectance Sp, which is a ratio between the amplitudes of the forward wave and the receding wave, is expressed through Formula (19).

$$S_p = \frac{P_r}{P_f} = \frac{Z_x - Z_0}{Z_x + Z_0} = \frac{1 - \frac{Z_0}{Z_x}}{1 + \frac{Z_0}{Z_x}} \tag{19}$$

Calculation of Vertical Impedance

A vertical impedance Z1 is made up of the nonelastic resistance of a fluid and a term of inertia, and is found by modeling a flow speed distribution within a blood vessel cross-section.

In the verifications, the vertical impedance was calculated based on the Womersley model. The Womersley model expresses a flow speed distribution in a state in which pulsatile flow in a Newtonian fluid has sufficiently progressed within a circular tube. The vertical impedance based on this Womersley model is expressed through Formula (20), using a Bessel function of the first kind Jn.

$$Z_l = \frac{j\omega\frac{\rho}{\pi r_i^2}}{1 - \frac{2J_1(\alpha\sqrt{-j})}{\alpha\sqrt{-j}J_0(\alpha\sqrt{-j})}} \tag{20}$$

(where $\rho$ represents the density of the blood, $r_i$ represents the inner diameter of the tube, and $\mu$ represents a viscosity coefficient of the blood)

$$\alpha = \sqrt{r_i^2 \pi \omega/\mu}$$

Here, $\alpha$ in Formula (20) is called the "Womersley alpha", and is an amount indicating a ratio between a viscosity term and an inertia term in a pulsatile flow; the number corresponds to the Reynolds number during steady flow. The blood density $\rho$ is typically taken as $1.03\times10^3$(kg/m$^3$), whereas a viscosity coefficient $\mu$ of the blood is typically taken as $4\times10^{-3}$ (Pa/s).

Note that a nonviscous model may be used instead of the Womersley model indicated in Formula (20). This model takes the blood as a nonviscous fluid, and assumes a constant flow speed in a cross-section. The vertical impedance based on this nonviscous model is expressed through Formula (21).

$$Z_l = j\omega\frac{\rho}{A} \tag{21}$$

Furthermore, the Poiseuille model may be used instead of the above models. This model expresses a flow speed distribution in a state in which a steady flow in a Newtonian fluid has sufficiently progressed within a circular tube. The vertical impedance based on the Poiseuille model is expressed through Formula (22).

$$Z_l = \frac{8\mu}{\pi r_i^4} + j\omega\frac{\rho}{\pi r_i^2} \tag{22}$$

Calculation of Horizontal Impedance

The horizontal impedance is configured of a leakage or branching term G and a tube compliance term C.

With respect to the leakage or branching term, G=0 in the case where there is no leakage or branching from the blood vessel walls to the surrounding structures. However, in the case where there is branching, the admittance of the branching tubes is taken as G.

Next, with respect to the tube compliance term, a compliance that models a thick-walled circular tube can be used. The compliance of an axially-symmetrical minute deformation in a thick-walled circular tube under set conditions of external pressure and strain in the axial direction is expressed by Formula (23).

$$C = \frac{dA}{dP} = \frac{2\pi r_i^2 (1-v)}{E} \cdot \frac{r_i^2(1-2v) + r_o^2}{r_o^2 - r_i^2} \quad (23)$$

(where E represents the Young's modulus of the blood vessel wall, v represents the Poisson ratio of the blood vessel wall, $r_i$ represents the inner diameter of the blood vessel, and $r_o$ represents the outer diameter of the blood vessel)

Here, the Poisson ratio v of the blood vessel wall is typically 0.5.

Note that a compliance that models a thin-walled circular tube may be used instead of the compliance that models the thick-walled circular tube as expressed by Formula (23). This compliance of an axially-symmetrical minute deformation in a thin-walled circular tube under set conditions of external pressure and strain in the axial direction is expressed by Formula (24).

$$C = \frac{dA}{dP} = \frac{2\pi r_i^3 (1-v^2)}{Eh} \quad (24)$$

(where h represents the vessel wall thickness)

Using the Avolio model as a circulatory system model, the inventors calculated the vertical impedance and horizontal impedance for each segment using Formulas (20) and (23). Furthermore, using the calculated vertical impedance and horizontal impedance, the inventors calculated transfer matrices for each segment in accordance with Formulas (15), (16), and (17), and by connecting each transfer function in cascade or in parallel in association with the actual connection relationships in each segment, calculated a pulse wave transmission model (transfer function) for the entire body using the heart as a base point. To be more specific, the two-row by two-column transfer matrices indicated by Formula (17) are connected in sequence according to the connection relationships of the respective segments (continuity, branching, endpoints, and so on).

In the Avolio model, the area indicated by the circled A expresses the measurement area on which the pressure cuff 24a is worn (a lower limb), the area indicated by the circled B expresses the measurement area on which the pressure cuff 24b is worn (an upper limb), and the area indicated by the circled C expresses an area in which it is assumed that an arterial aneurysm, serving as a predetermined pathologic change in the vascular pathway, has occurred. The inventors calculated the pulse wave velocity using the stated first calculation unit 32, and using the Avolio model as the circulatory system model, calculated a transfer function Ga(f) corresponding to the vascular pathway from the heart to the measurement area A and a transfer function Gb(f) corresponding to the vascular pathway from the heart to the measurement area B; then, using the results of those calculations, the inventors calculated a slope g(k) of the phase line. The slope g(k) (deg/Hz) of the phase line can be defined as the slope g(k)=tan(φmodel), using a declination φmodel calculated as the declination φmodel=∠ transfer function Ga(f)/transfer function Gb(f).

Note that a slope g(k1) of the phase line in the case where the pulse wave velocity (PWV) calculated by the stated first calculation unit 32 is verified is calculated using the transfer functions Ga(f) and Gb(f) in a frequency band of 10 Hz to 20 Hz, which has been shown in advance not to be influenced by a predetermined pathologic changes in the vascular pathway. Then, the pulse wave velocity (PWV) is calculated by dividing the difference ΔL in the distance of the vascular pathway from the heart to the measurement area A and the distance of the vascular pathway from the heart to the measurement area B, which have been defined in advance, by the propagation time difference Td obtained as the slope g(k1) of the phase line.

Analysis Results

FIGS. 11A through 11D are graphs illustrating a result of analyzing the evaluation performed by the measurement apparatus 100A. FIGS. 11A through 11D express, for cases 1 through 4, a ratio of the pulse wave velocity (PWV) calculated by obtaining the appearance time differences at the respective predetermined locations of a typical pulse waveform measured at the aforementioned measurement areas as the propagation time difference Td and dividing the difference ΔL in the pre-set distances of the respective vascular pathways from the heart to the measurement areas on which the pressure cuffs 24a and 24b are worn by the calculated propagation time difference Td, to the pulse wave velocity (PWV) calculated by dividing the stated distance difference ΔL by the slope g(k1) of the phase line calculated using the transfer functions Ga(f) and Gb(f) in the 10 Hz to 20 Hz range using the Avolio model.

Figure 11A:
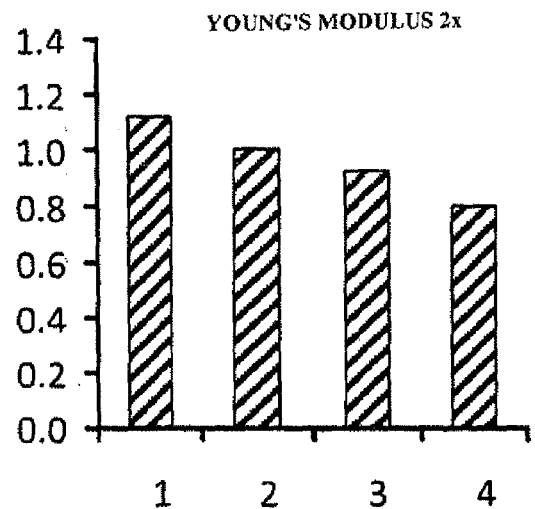
FIG. 11A is a graph illustrating a result of analyzing evaluations made by the measurement apparatus according to the first embodiment.
Figure 11B:
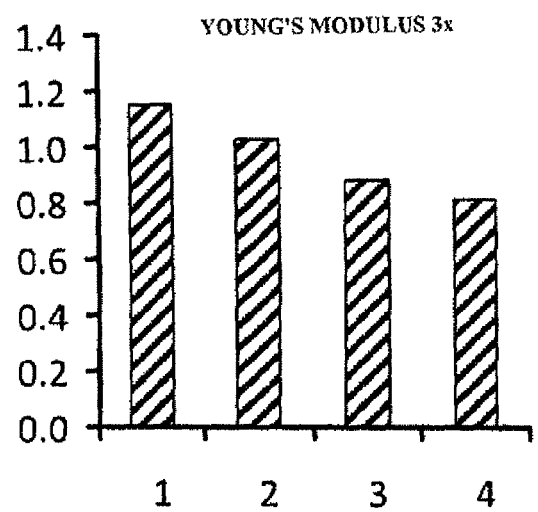
FIG. 11B is a graph illustrating a result of analyzing evaluations made by the measurement apparatus according to the first embodiment.
Figure 11C:
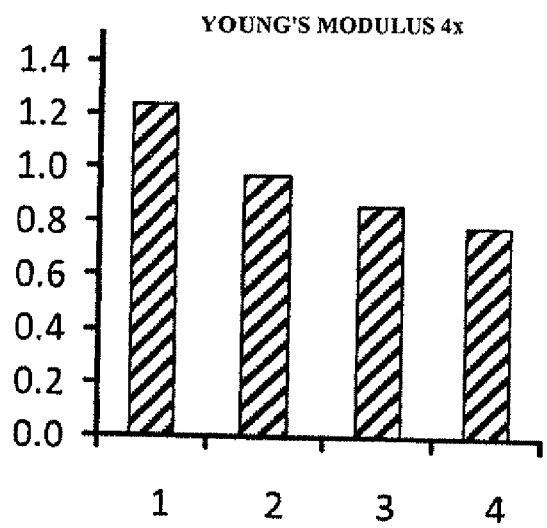
FIG. 11C is a graph illustrating a result of analyzing evaluations made by the measurement apparatus according to the first embodiment.
Figure 11D:
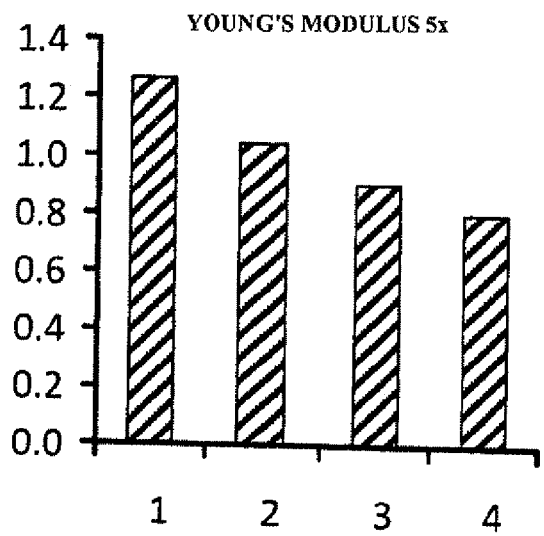
FIG. 11D is a graph illustrating a result of analyzing evaluations made by the measurement apparatus according to the first embodiment.

Case 1 is a model in the case where the blood vessel diameter is 5.7 (mm) and no arterial aneurysm is present; case 2 is a model in the case where the blood vessel diameter is 10 (mm) and an arterial aneurysm is present; case 3 is a model in the case where the blood vessel diameter is 15 (mm) and an arterial aneurysm is present; and case 4 is a model in the case where the blood vessel diameter is 20 (mm) and an arterial aneurysm is present. In addition, FIG. 11A expresses the ratio in the case where the pulse wave velocity (PWV) has been calculated using a Young's modulus that is twice the base value of the Avolio model; FIG. 11B expresses the ratio in the case where the pulse wave velocity (PWV) has been calculated using a Young's modulus that is three times the base value; FIG. 11C expresses the ratio in the case where the pulse wave velocity (PWV) has been calculated using a Young's modulus that is four times the base value; and FIG. 11D expresses the ratio in the case where the pulse wave velocity (PWV) has been calculated using a Young's modulus that is five times the base value.

From the analysis results indicated in FIGS. 11A through 11D, it was shown through simulations that regardless of the Young's modulus, or in other words, regardless of individual differences in blood vessel states, the aforementioned ratio is lower in the case where an arterial aneurysm is present than in the case where an arterial aneurysm is not present, and that the greater the blood vessel diameter, the lower the stated ratio will become.

Verification 1 through Actual Measurement

The inventors carried out measurements using the measurement apparatus 100A on a measurement subject group in which arterial aneurysms were not present and a measurement subject group in which arterial aneurysms were present, and compared the pulse wave velocity (PWV) calculated by the first calculation unit 32 with the pulse wave velocity (PWV) calculated by the second calculation unit 38.

Figure 12A:
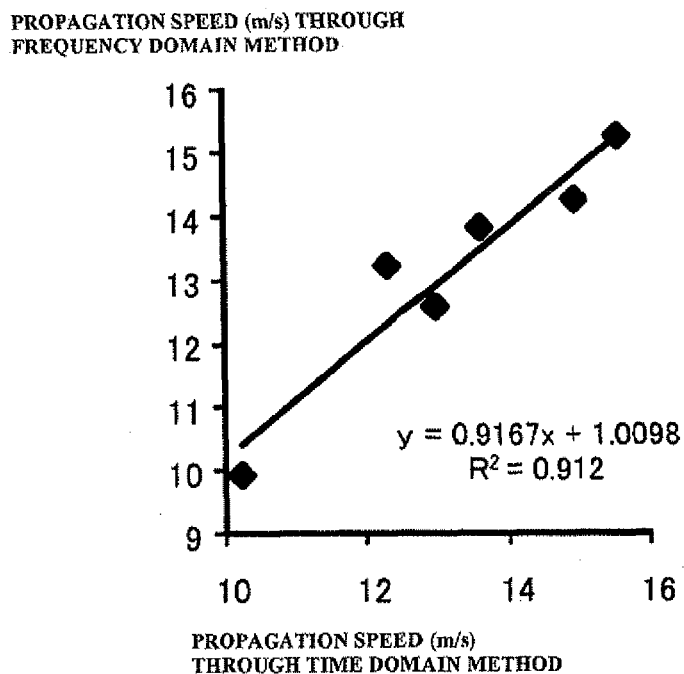
FIG. 12A is a graph illustrating a result of a comparison made with a measurement subject group that does not have arterial aneurysms.
Figure 12B:
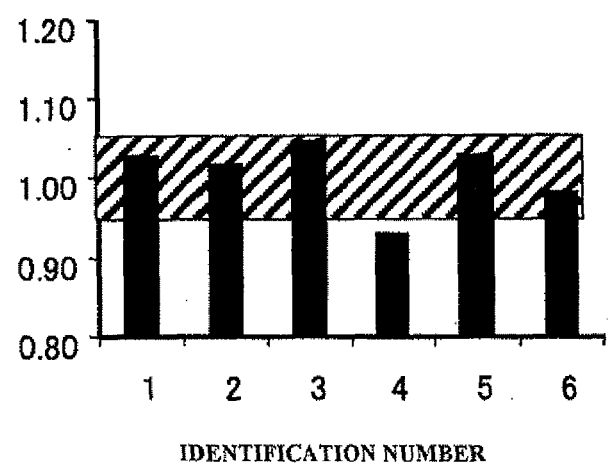
FIG. 12B is a graph illustrating a result of a comparison made with a measurement subject group that does not have arterial aneurysms.
Figure 13:
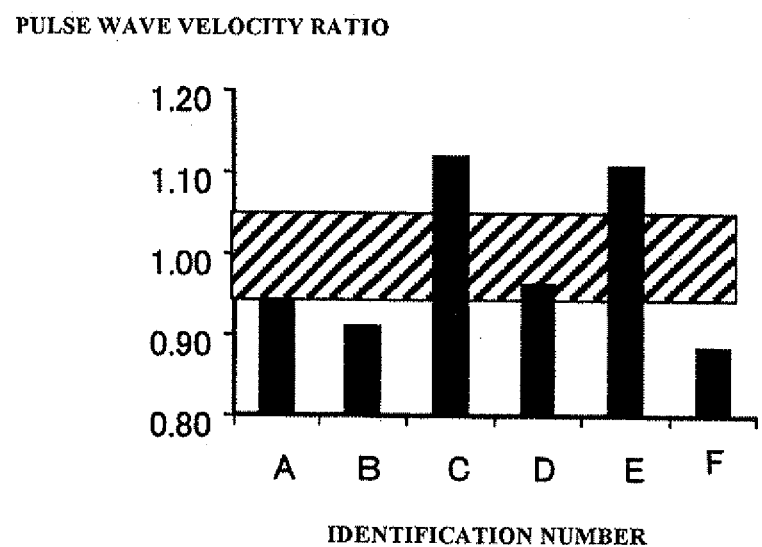
FIG. 13 is a graph illustrating a result of a comparison made with a measurement subject group that has arterial aneurysms.

FIGS. 12A and 1213 illustrate results of the comparisons for the measurement subject group in which arterial aneurysms were not present; FIG. 12A illustrates a pulse wave velocity (PWV) distribution calculated by the first calculation unit 32 for the pulse wave velocity (PWV) calculated by the second calculation unit 38, whereas FIG. 12B illustrates a ratio of the pulse wave velocity (PWV) calculated by the first calculation unit 32 to the pulse wave velocity (PWV) calculated by the second calculation unit 38 for each measurement subject. FIG. 13, meanwhile, is a graph illustrating a result of a comparison made with a measurement subject group in which arterial aneurysms are present.

As shown in FIGS. 12A and 1213, in the case where no arterial aneurysm is present, the ratio of the pulse wave velocity (PWV) calculated by the first calculation unit 32 to the pulse wave velocity (PWV) calculated by the second calculation unit 38 is highly likely to be within a predetermined range (1±0.05). Accordingly, it was verified that, in the case where no arterial aneurysm is present, the pulse wave velocity (PWV) calculated by the first calculation unit 32 can be called essentially equal to the pulse wave velocity (PWV) calculated by the second calculation unit 38.

On the other hand, as shown in FIG. 13, in the case where an arterial aneurysm is present, measurement results in which the ratio of the pulse wave velocity (PWV) calculated by the first calculation unit 32 to the pulse wave velocity (PWV) calculated by the second calculation unit 38 is scattered outside of the predetermined range (1.00±0.05) were obtained more than in the case where an arterial aneurysm was not present.

Through this, it was verified that the ratio of the pulse wave velocity (PWV) calculated by the first calculation unit 32 to the pulse wave velocity (PWV) calculated by the second calculation unit 38 tends to be scattered outside of the predetermined range (1.00±0.05) more than in the case where an arterial aneurysm is present.

Verification 2 through Actual Measurement

Figure 14A:
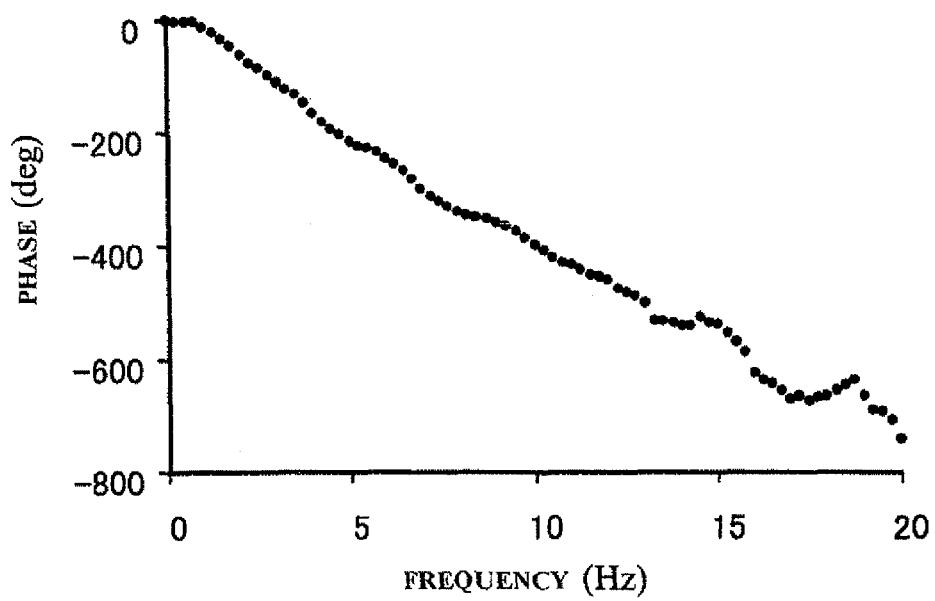
FIG. 14A is a diagram illustrating a specific example of a phase diagram obtained when plotting phase differences in respective frequency components between the measurement signal Pa(t) and the measurement signal Pb(t) from the respective measurement areas.
Figure 14B:
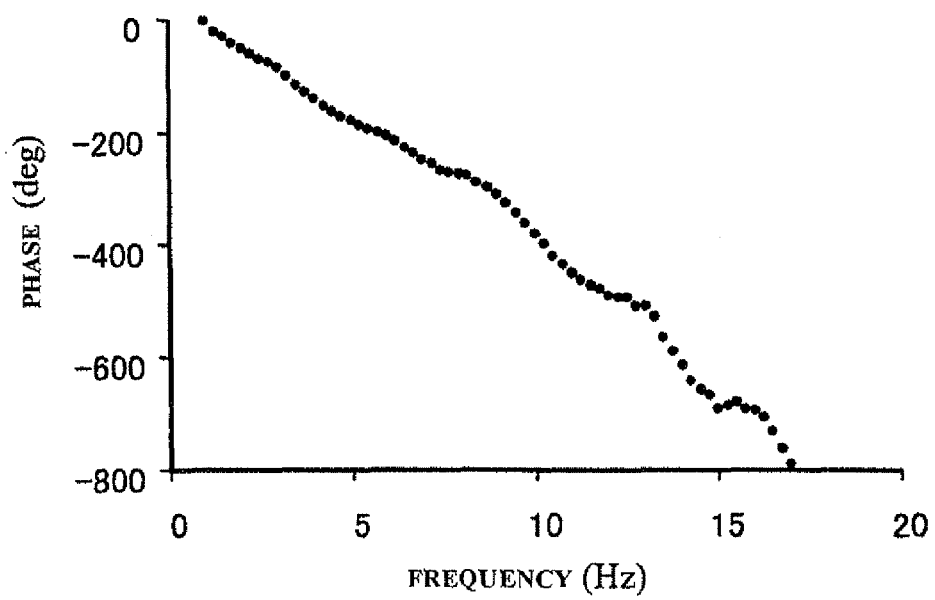
FIG. 14B is a diagram illustrating a specific example of a phase diagram obtained when plotting phase differences in respective frequency components between the measurement signal Pa(t) and the measurement signal Pb(t) from the respective measurement areas.
Figure 14C:
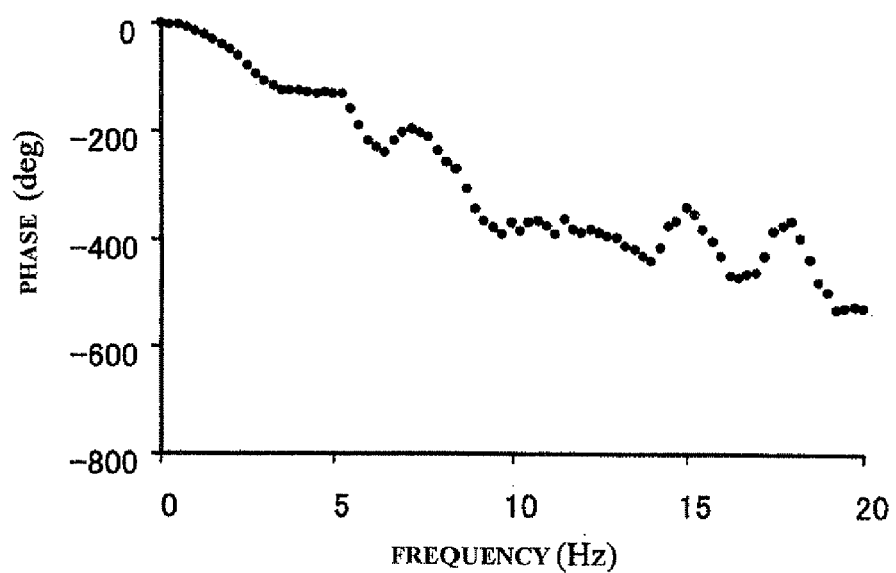
FIG. 14C is a diagram illustrating a specific example of a phase diagram obtained when plotting phase differences in respective frequency components between the measurement signal Pa(t) and the measurement signal Pb(t) from the respective measurement areas.

FIGS. 14A through 14C are diagrams illustrating specific examples of phase diagrams obtained when plotting phase differences in respective frequency components between the measurement signal Pa(t) and the measurement signal Pb(t), and are specific examples of phase diagrams in which the aforementioned correction has been carried out on the discontinuous points with a ±180° boundary. FIGS. 14A, 14B, and 14C show phase diagrams obtained based on the measurement signals Pa(t) and Pb(t) measured from different measurement subjects.

Figure 15A:
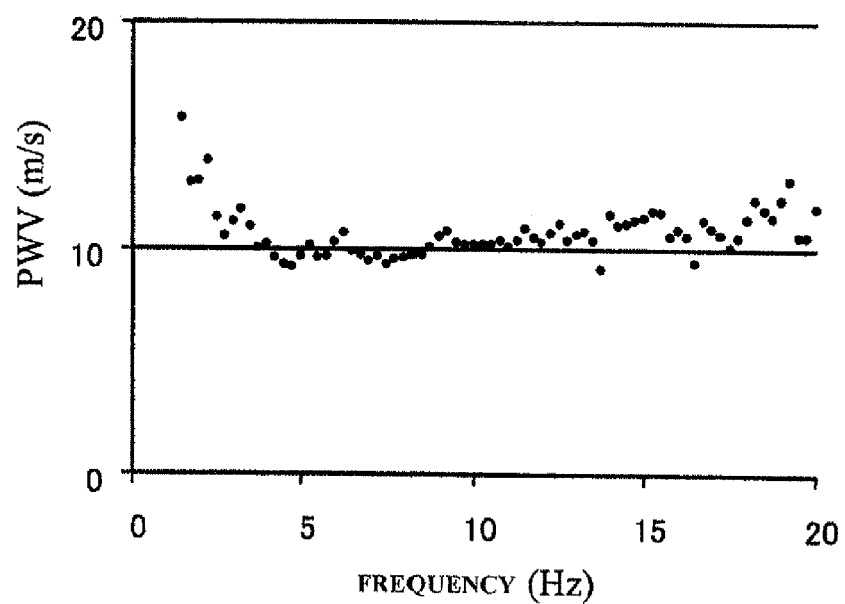
FIG. 15A illustrates a pulse wave velocity (PWV) calculated from the phase differences shown in the phase diagram in FIG. 14A.
Figure 15B:
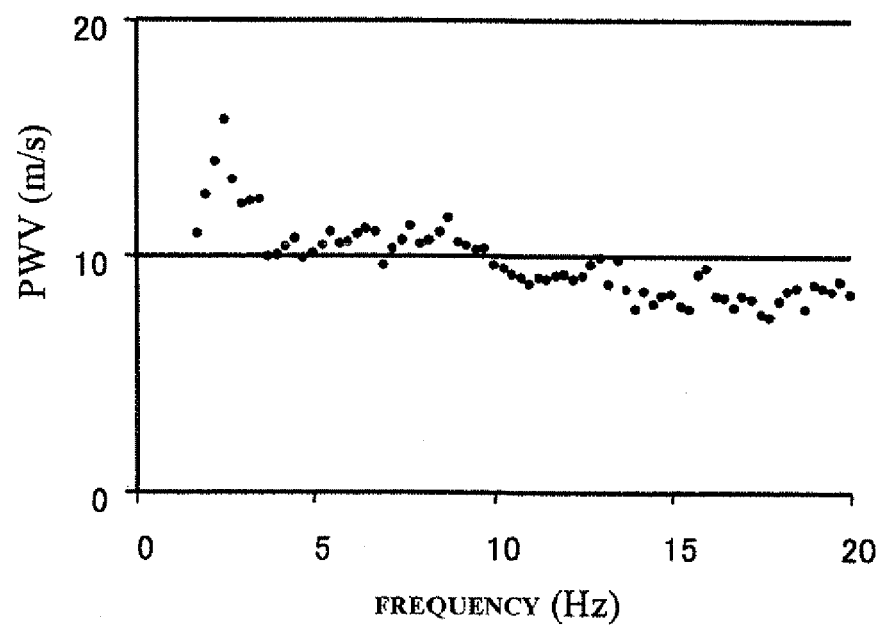
FIG. 15B illustrates a pulse wave velocity (PWV) calculated from the phase differences shown in the phase diagram in FIG. 14B.
Figure 15C:
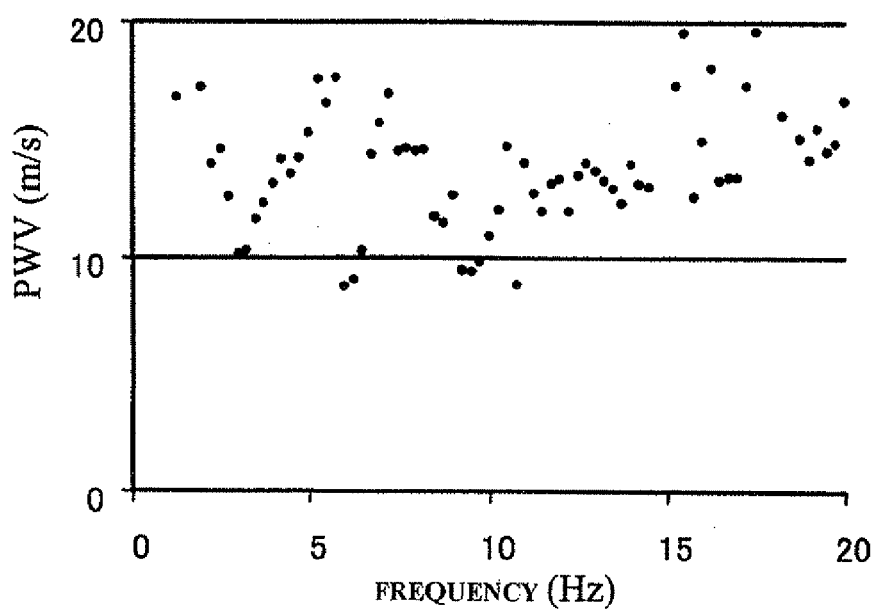
FIG. 15C illustrates a pulse wave velocity (PWV) calculated from the phase differences shown in the phase diagram in FIG. 14C.

Meanwhile, FIGS. 15A through 15C are diagrams illustrating specific examples of the pulse wave velocity (PWV) calculated from the phase difference in respective frequency components. FIGS. 15A, 15B, and 15C express the pulse wave velocities (PWV) calculated from the phase differences expressed by the phase diagrams in FIGS. 14A, 14B, and 14C, respectively.

With the phase diagrams illustrated in FIGS. 14A and 14B, it is possible to compare slopes of regression lines for 0 Hz to 10 Hz and 10 Hz and 20 Hz, respectively. Accordingly, in such a case, as shown in FIGS. 15A and 15B, pulse wave velocities (PWV) based on the slopes of the regression lines obtained in the respective ranges are obtained. Accordingly, in such a case, it is possible to accurately evaluate whether or not a predetermined pathologic change such as an arterial aneurysm is present using the aforementioned measurement apparatus 100B that carries out the evaluation based on these ratios.

On the other hand, with the phase diagram illustrated in FIG. 14C, there is a high level of noise, and thus trends in the slopes of the regression lines in the respective frequency bands do not appear clearly. In this case, as shown in FIG. 15C, trends in the pulse wave velocities (PWV) calculated from the respective phase differences do not appear clearly in the respective frequency bands. Accordingly, in such a case, it is possible that the aforementioned measurement apparatus 100B, which carries out evaluation based on the ratios of the pulse wave velocities (PWV) in the respective frequency bands, cannot accurately evaluate whether or not a predetermined pathologic change such as an arterial aneurysm is present. Accordingly, in such a case, whether or not a predetermined pathologic change such as an arterial aneurysm is present can be more accurately evaluated using the aforementioned measurement apparatus 100A, which carries out evaluation based on the ratio of the pulse wave velocity (PWV) calculated by obtaining the propagation time difference Td from the appearance time difference in predetermined positions of the pulse waveform obtained by rendering the measurement signals Pa(t) and Pb(t) on respective time axes, to the pulse wave velocity (PWV) calculated from the phase difference between the measurement signal Pa(t) and the measurement signal Pb(t) in the high-frequency components thereof.

Therefore, as another embodiment, the measurement apparatus 100A and the measurement apparatus 100B may be combined, and the CPU 10 may switch between the calculation method of the second calculation unit 38 and the calculation method of the third calculation unit 39 in accordance with the shape of the phase diagram obtained by plotting the phase difference between the measurement signal Pa(t) and the measurement signal Pb(t) for the respective frequency components.

Other Embodiments

Furthermore, a program can be provided for realizing the method for evaluating the presence of a predetermined pathologic change such as an arterial aneurysm carried out by the measurement apparatus according to the aforementioned embodiment. Such a program can be recorded on a computer-readable recording medium such as a flexible disk, a CD-ROM (compact disk read-only memory), a ROM, a RAM, a memory card, or the like that is read by a computer, and can be provided as a program product. Alternatively, the program can be recorded on a recording medium such as a hard disk mounted within a computer, and can be provided in such form as a program. Further still, the program can also be downloaded via a network, and can be provided in such form as a program.

Note that the program according to the present invention may execute processing by calling, in a predetermined arrangement and at a predetermined timing, the necessary program modules from among the modules provided as part of an operating system (OS) of a computer. In this case, the stated modules are not included in the program itself, and the processing is executed in cooperation with the OS. Such a program that does not include modules in this manner can also fall within the scope of the program according to the present invention.

In addition, the program according to the present invention may be provided having been incorporated into a part of another program. In such a case as well, modules included in the stated other program are not included within the program itself, and the processing is executed in cooperation with the other program. Such a program that is incorporated into another program can also fall within the scope of the program according to the present invention.

The program product that is provided is installed in a program storage unit such as a hard disk and executed. Note that the program product includes the program itself and the recording medium on which the program is recorded.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A measurement apparatus for use with a measurement subject including a body having a body surface, a heart, a first vascular pathway and a second vascular pathway, the measurement apparatus comprising:
 a first blood pressure measurement cuff configured to be worn on a first measurement area that corresponds to the body surface at an area to which blood travels from the heart through the first vascular pathway, the first measurement cuff being configured to measure a first pulse wave signal;
 a second blood pressure measurement cuff configured to be worn on a second measurement area that corresponds to the body surface at an area to which blood travels from the heart through the second vascular pathway, the second blood pressure measurement cuff being configured to measure a second pulse wave signal; and
 a controller including a processor operatively coupled to a memory, the memory storing a program executed by the processor, the controller being configured to:
  convert the first pulse wave signal and the second pulse wave signal into a first frequency component and a second frequency component;
  calculate a first pulse wave velocity based on subsets of the first frequency component and the second frequency component in first frequencies that have been shown in advance not to be influenced by a predetermined pathologic change in the second vascular pathway;
  calculate a second pulse wave velocity based on subsets of the first frequency component and the second frequency component in second frequencies that have been shown in advance to be influenced by the predetermined pathologic change in the second vascular pathway;
  compare the first pulse wave velocity and the second pulse wave velocity in order to determine a difference between the first pulse wave velocity and the second pulse wave velocity;
  determine whether the difference between the first pulse wave velocity and the second pulse wave velocity exceeds a predetermined threshold value; and
  generate and transmit a signal to a display that displays: (i) an evaluation result of a degree to which the first pulse wave velocity and the second pulse wave velocity match, and (ii) the determination of whether the difference between the first pulse wave velocity and the second pulse wave velocity exceeds the predetermined threshold value, in order to evaluate a likelihood of a pathologic change in a vascular pathway from the heart to the first measurement area and the second measurement area.

2. The measurement apparatus according to claim 1, wherein the calculation of the first pulse wave velocity includes calculating the first pulse wave velocity based on a phase difference between said first pulse wave signal and the second pulse wave signal at the first frequencies, the first frequencies, and a difference between a distance from the heart to the first measurement area and a distance from the heart to the second measurement area.

3. The measurement apparatus according to claim 1, wherein the calculation of the second pulse wave velocity includes calculating the second pulse wave velocity based on a propagation time difference obtained by comparing a predetermined position in a pulse wave shape obtained by rendering the first pulse wave signal on a time axis with a predetermined position in a pulse wave shape obtained by rendering the second pulse wave signal on a time axis, and based on a difference between a distance from the heart to the first measurement area and a distance from the heart to the second measurement area.

4. The measurement apparatus according to claim 1, wherein the calculation of the second pulse wave velocity includes calculating the second pulse wave velocity based on a phase difference in pulse waves in second frequencies.

5. A computer-implemented measurement method for use with a measurement subject including a body having a body surface, a heart, a first vascular pathway and a second vascular pathway, the computer-implemented measurement method comprising:
 measuring a first pulse wave signal at a first measurement area that corresponds to the body surface at an area to which blood travels from the heart through the first vascular pathway;
 measuring a second pulse wave signal at a second measurement area that corresponds to the body surface at an area to which blood travels through the second vascular pathway;
 converting the first pulse wave signal and the second pulse wave signal into a first frequency component and a second frequency component;
 calculating a first pulse wave velocity based on subsets of the first frequency component and the second frequency component in first frequencies that have been shown in advance not to be influenced by a predetermined pathologic change in the second vascular pathway;
 calculating a second pulse wave velocity based on subsets of the first frequency component and the second frequency component in second frequencies that have been shown in advance to be influenced by the predetermined pathologic change in the second vascular pathway;
 comparing the first pulse wave velocity and the second pulse wave velocity in order to determine a difference between the first pulse wave velocity and the second pulse wave velocity;
 determining whether the difference between the first pulse wave velocity and the second pulse wave velocity exceeds a predetermined threshold value; and
 generating and transmitting a signal to a display that displays: (i) an evaluation result of a degree to which the first pulse wave velocity and the second pulse wave velocity match, and (ii) the determination of whether the difference between the first pulse wave velocity and the second pulse wave velocity exceeds the predetermined threshold value, in order to evaluate a likelihood of a pathologic change in a vascular pathway from the heart to the first measurement area and the second measurement area.

6. The measurement apparatus according to claim 1, wherein the output of the degree includes outputting the degree as a likelihood of the predetermined pathologic change in the second vascular pathway.

7. The computer-implemented measurement method according to claim 5, wherein the calculation of the first pulse wave velocity includes calculating the first pulse wave velocity based on a phase difference between the first pulse wave signal and the second pulse wave signal at the first frequencies, the first frequencies, and a difference between a distance from the heart to the first measurement area and a distance from the heart to the second measurement area.

8. The computer-implemented measurement method according to claim 5, wherein the calculation of the second pulse wave velocity includes calculating the second pulse wave velocity based on a propagation time difference obtained by comparing a predetermined position in a pulse wave shape obtained by rendering the first pulse wave signal on a time axis with a predetermined position in a pulse wave shape obtained by rendering the second pulse wave signal on a time axis, and based on a difference between a distance from the heart to the first measurement area and a distance from the heart to the second measurement area.

9. The computer-implemented measurement method according to claim 5, wherein the calculation of the second pulse wave velocity includes calculating the second pulse wave velocity based on a phase difference in pulse waves in second frequencies.

10. The computer-implemented measurement method according to claim 5, wherein the output of the degree includes outputting the degree as a likelihood of the predetermined pathologic change in the second vascular pathway.

* * * * *